(12) United States Patent
Hancock

(10) Patent No.: US 8,795,267 B2
(45) Date of Patent: Aug. 5, 2014

(54) SURGICAL RESECTION APPARATUS

(75) Inventor: Christopher Paul Hancock, Bristol (GB)

(73) Assignee: Creo Medical Limited, Chepstow (GB)

( * ) Notice: Subject to any disclaimer, the term of this patent is extended or adjusted under 35 U.S.C. 154(b) by 837 days.

(21) Appl. No.: 12/679,784

(22) PCT Filed: Sep. 24, 2008

(86) PCT No.: PCT/GB2008/003235
§ 371 (c)(1),
(2), (4) Date: Mar. 24, 2010

(87) PCT Pub. No.: WO2009/040523
PCT Pub. Date: Apr. 2, 2009

(65) Prior Publication Data
US 2010/0286686 A1     Nov. 11, 2010

(30) Foreign Application Priority Data

Sep. 25, 2007   (GB) .................................. 0718721.4

(51) Int. Cl.
*A61B 18/18*       (2006.01)
*A61B 17/3211*     (2006.01)

(52) U.S. Cl.
CPC ............. *A61B 18/18* (2013.01); *A61B 17/3211* (2013.01); *A61B 18/1815* (2013.01)
USPC .............................................. 606/33; 606/45

(58) Field of Classification Search
CPC .................... A61B 17/3211; A61B 18/1815
USPC ................ 606/33, 39, 45; 607/101, 154, 156
See application file for complete search history.

(56) References Cited

U.S. PATENT DOCUMENTS 4,534,347 A      8/1985  Taylor
5,349,700 A  *   9/1994  Parker ..................... 455/193.2
(Continued)

FOREIGN PATENT DOCUMENTS

CN          85105972 A     2/1987
CN          1103807 A      6/1995
(Continued)

OTHER PUBLICATIONS

Ninnis, Tom, "Microwave Power Modules: Minature Microwave Amplifiers for UAVs", L-3 Communications Corporation, Dec. 2003.

(Continued)

*Primary Examiner* — Linda Dvorak
*Assistant Examiner* — Jocelyn D Ram
(74) *Attorney, Agent, or Firm* — Arent Fox LLP

(57) ABSTRACT

Surgical cutting apparatus having a treatment channel and a measurement channel for conveying microwave energy from a source to an antenna at a cutting edge. The measurement channel operates at lower power than the treatment channel for determining when higher energy can be safely applied. The apparatus may deliver microwave radiation at differing frequencies to one or more antennas at the cutting edge, e.g. to provide different treatment effects. The source may generate an output for an antenna whose frequency can be selected e.g. for most efficient operation. Selection may be automatic based on detected magnitude and phase of reflected signals during a frequency sweep of a forward signal. Power delivered to tissue via the cutting element may be manually boosted to deal with large blood vessels. The apparatus may include a reflected power monitor for recognizing behavior in reflected signals received from the antenna to trigger automatic pre-emptive action.

14 Claims, 10 Drawing Sheets

(56) References Cited

U.S. PATENT DOCUMENTS

| | | | |
|---|---|---|---|
| 5,370,675 A | 12/1994 | Edwards et al. | |
| 5,542,916 A * | 8/1996 | Hirsch et al. | 604/22 |
| 5,800,494 A * | 9/1998 | Campbell et al. | 607/116 |
| 6,067,475 A * | 5/2000 | Graves et al. | 607/101 |
| 6,221,069 B1 | 4/2001 | Daikuzono | |
| 8,515,554 B2 * | 8/2013 | Carr | 607/101 |
| 2002/0156511 A1 | 10/2002 | Habib | |
| 2005/0143795 A1 | 6/2005 | Habib et al. | |
| 2005/0171534 A1 | 8/2005 | Habib | |
| 2006/0047274 A1 | 3/2006 | Habib et al. | |
| 2006/0155270 A1 * | 7/2006 | Hancock et al. | 606/33 |
| 2007/0121267 A1 * | 5/2007 | Kotani et al. | 361/85 |
| 2007/0299488 A1 * | 12/2007 | Carr | 607/101 |
| 2008/0234574 A1 * | 9/2008 | Hancock et al. | 600/430 |
| 2010/0030207 A1 | 2/2010 | Hancock | |
| 2010/0087808 A1 * | 4/2010 | Paulus | 606/33 |
| 2010/0121318 A1 * | 5/2010 | Hancock et al. | 606/33 |
| 2010/0286687 A1 * | 11/2010 | Feldberg et al. | 606/33 |
| 2011/0054458 A1 * | 3/2011 | Behnke | 606/33 |
| 2011/0125148 A1 * | 5/2011 | Turner et al. | 606/33 |
| 2011/0208177 A1 * | 8/2011 | Brannan | 606/33 |
| 2011/0208179 A1 * | 8/2011 | Prakash et al. | 606/33 |
| 2012/0203218 A1 * | 8/2012 | Bonn | 606/33 |
| 2012/0253341 A1 * | 10/2012 | Paulus | 606/33 |
| 2012/0303017 A1 * | 11/2012 | Brannan et al. | 606/33 |

FOREIGN PATENT DOCUMENTS

| | | |
|---|---|---|
| CN | 1302588 A | 7/2001 |
| JP | 08-168493 | 7/1996 |

OTHER PUBLICATIONS

Chinese Search Report.

* cited by examiner

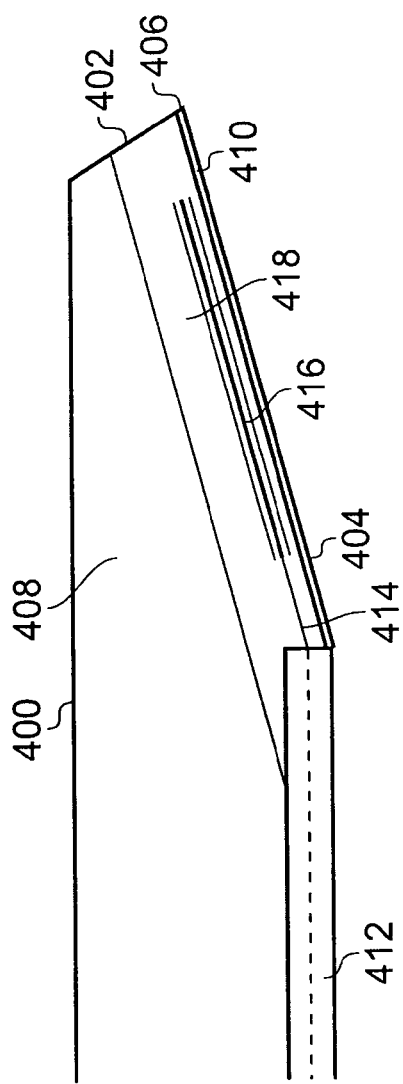
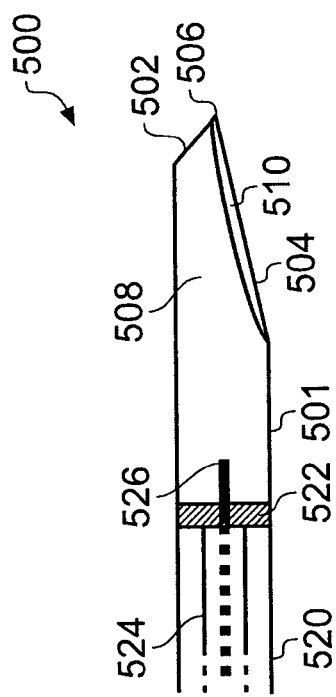
FIG. 4
FIG. 5

SURGICAL RESECTION APPARATUS

CROSS-REFERENCE TO RELATED APPLICATION

This application is a National Stage entry of International Application No. PCT/GB2008/003235, international filing date Sep. 24, 2008, which claims priority to GB Patent Application No. 0718721.4 filed Sep. 25, 2007, the disclosure of each of which is hereby incorporated by reference in its entirety.

TECHNICAL FIELD

This application relates to surgical resection apparatus which is arranged to controllably deliver microwave energy into biological tissue.

BACKGROUND TO THE INVENTION

The disclosure herein builds on the content of the applicant's earlier UK patent application no. 0620060.4, filed on 10 Oct. 2006. That document describes a surgical cutting e.g. resection apparatus comprising a source of microwave radiation that is coupled to a surgical instrument having an antenna associated with a blade for cutting biological tissue, wherein the antenna is arranged to controllably deliver microwave energy from the source to a region where the blade cuts through tissue. The microwave energy can coagulate blood to effectively seal off the blood flow at the cutting region. Such an effect may be particularly beneficial when performing surgery on highly vascularised organs such as the liver or spleen.

The use of high microwave frequencies (e.g. 10 GHz or higher) offers particular advantage over the use of lower microwave frequency systems and RF systems due to the limited depth of penetration of the energy by radiation and the ability to enable small sharp blade structures to efficiently radiate energy into the tissue to seal off blood flow by being able to produce uniform fields along the length of the blade whilst at the same time being capable of cutting through the tissue to remove sections of diseased or cancerous tissue. The higher the microwave frequency, the more localised the energy distribution becomes and the energy density at the site where the cutting action takes place is correspondingly high, hence the easier it becomes to effectively seal off blood flow as the cutting blade is introduced into highly perfused biological tissue structures. The ability to localise the distribution of energy is advantageous in terms of limiting the amount of damage caused to healthy tissue. This feature may be particularly advantageous where it is required to remove large sections of diseased liver, where it is of paramount importance to save as much of the organ or healthy tissue as possible. A substantially uniform field profile can enable uniform coagulation or other tissue effects along the cutting edge. Using lower frequency microwave energy (e.g. 1 GHz or less) can lead to non-radiating regions of the antenna, which reduces the ability of the device to produce effective coagulation. By emitting a uniform field of microwave energy having a suitable energy density along the edge of the blade, the wound is effectively sealed as the surgeon cuts through the tissue structure.

In this specification microwave means the frequency range of between 2 GHz and 100 GHz, but preferably between 10 GHz and 25 GHz, and even more preferably between 14 GHz and 24 GHz. For example, spot frequencies of 14.5 GHz or 24 GHz may be used.

Higher frequencies (e.g. 24 GHz) may provide advantages such as a smaller size waveguide cable assembly, a smaller size antenna, i.e. the blade may be made to look similar in appearance and have the same physical dimensions as a standard scalpel blade, and smaller depth of penetration at lower frequencies (e.g. 14.5 GHz). For example, in liver at 24 GHz the depth of penetration is 1.1 mm, whereas it is 2 mm at 14.5 GHz. The smaller depth of penetration may permit higher energy density and more instant seal or coagulation to take place as the blade cuts into the tissue.

UK patent application no. 0620060.4 disclosed that a radiating section of the antenna may be dynamically tuned or impedance matched to a changing tissue load impedance (i.e. the distal tip of the radiating blade or structure may be adjusted to be the complex conjugate of the complex impedance of the treatment tissue) in order to optimise the level of power delivered into the tissue and to minimise reflected power. Additionally it was disclosed that the antenna may be arranged to enable measurements of tissue characteristics to be taken, e.g. using a treatment system as disclosed in WO 2004/047659 or WO 2005/115235.

SUMMARY OF THE INVENTION

The disclosure herein presents a number of features, each of which can be implemented, either alone or in any combination, in the surgical apparatus discussed above.

Selectable Channels

In a first aspect, the apparatus may be arranged to provide a treatment channel and a measurement channel which are different paths for microwave energy from the source to the antenna. The measurement channel may provide energy at a lower power level than the treatment channel to permit a determination of when the higher energy from the treatment channel can be safely applied, e.g. a level of reflected signal may be established first under low power conditions and if it is found that the microwave energy is being absorbed into the tissue load then the high power source can be activated.

Thus, according to the first aspect, there may be provided surgical cutting apparatus having a microwave radiation source arranged to generate microwave radiation; a surgical instrument having a cutting element with an edge for cutting biological tissue, and an antenna connected to the source and arranged to emit a substantially uniform microwave radiation field at the edge of the cutting element; and a reflected radiation detector arranged to receive signals reflected back from the antenna, wherein the antenna is selectively connectable to the source via a first channel for conveying a microwave signal at a first power level for treatment and a second channel for conveying a microwave signal at a second power level for measurement, and wherein the antenna is connected to the detector via a signal transfer unit which is arranged to route signals reflected from the antenna along the second channel directly to the detector.

As the reflected signals are provided directly to the detector in the measurement channel, the second power level can be lower. In contrast, where the reflected signals are provided indirectly, e.g. via couplers, the forward signal must be high enough to ensure that the coupled reflected signal is of high enough amplitude to be measurable. The power level required to achieve this may be sufficient to cause effects in the tissue, e.g. ablation or heating, which may be undesirable. The invention allows a safe level of microwave radiation to be delivered into the tissue. The detected signals from the 'safe' measurement channel may be used to decide when to use the higher power level for treatment. This safety feature may extend to limiting the power emitted by the device when in air.

For example, if the return loss of the antenna is limited to around 1 dB in air, this implies that if the delivered power is 80 W, then 63.55 W is reflected, but 16.45 W is radiated into free space. This situation is most undesirable.

The signal transfer unit may thus include a low power transceiver on the second channel to measure the reflected power levels in order to determine when the high power source should be activated. Such an arrangement can permit a travelling wave tube (TWT) or magnetron or other resonant cavity type structure to be used to generate the microwave power on the first channel. This type of device can be difficult to operate at power levels that are useful for making effective and safe measurements.

The first power level may be two or more orders of magnitude greater than the second power level. For example, the first power level may be up to 300 W; the second power level may be 100 mW or less.

Each channel may comprise a signal path for propagation of electromagnetic radiation. The channel may comprise a cable, e.g. a waveguide assembly, a co-axial cable or the like.

The first channel may include an amplifier connected between the source and the antenna to amplify the microwave radiation generated by the source to provide the microwave signal at the first power level. The second channel may bypass the amplifier. The signal generated at the second (lower) power level may therefore be more stable in terms of noise and signal amplitude/phase variation than the signal at the first (higher) power level, where signal distortion and other unwanted effects may be generated by the higher power device. This may be due to the fact that the components which comprise the major source of noise in the first channel are not required in the second channel. For example, the only sources of non-negligible noise in the second channel may be the source (e.g. a low power oscillator) and, optionally, a low noise amplifier e.g. to compensate for transmission losses along the second channel. If a low noise amplifier is included, it preferably has a noise figure of less than 3 dB.

The signal transfer unit may include a circulator connected between the source, the antenna and the detector on the second channel, the circulator being arranged to direct a forward signal from the source to the antenna and a reflected signal from the antenna to the detector. The circulator may therefore act as an isolator to separate the forward signal from the reflected signal. To minimize the effect of any leakage of the forward signal into the port connected to the detector, the signal transfer unit may include a carrier cancellation circuit connected to the circulator. For example, if a first port of the circulator is connected to the source, a second port to the antenna and a third port to the detector then the carrier cancellation circuit may be connected between the first and third ports. An example of a suitable carrier cancellation circuit that may be used is provided in UK patent application no. 0620064.6 filed on 10 Oct. 2006, and is incorporated by reference herein.

The signal transfer unit may include a directional coupler on the first channel, the directional coupler being arranged to couple a reflected signal from the antenna to the detector. The signal transfer unit may include a forward directional coupler (to measure a portion of the forward going power) and a backward directional coupler (to measure a portion of the reflected power) on the first channel, the directional couplers being respectively arranged to couple a forward signal from the source and a reflected signal from the antenna to the detector. The detected signals may be used to calculate the power delivered to the tissue or to compensate for the changes in impedance of the tissue at the radiating end of the antenna. The radiating antenna may be designed to be well matched to a particular tissue type, i.e. liver or spleen, that is in a particular state, e.g. cooked, partially cooked or uncooked.

The apparatus may include an impedance adjustor on the first channel, wherein the detector is arranged to detect the magnitude and phase of the reflected signal and the impedance adjustor has an adjustable complex impedance that is controllable based on the detected magnitude and phase. The first channel may therefore be arranged to match the impedance of the apparatus to the changing impedance of the load (tissue) to enable efficient power transfer. This may be useful as the impedance of blood will change as it is coagulated. The impedance matching may be dynamic, e.g. adjustment may occur automatically in real time.

The apparatus may include a switch arranged to connect the antenna to either the first channel or the second channel. The switch may be manually operable (e.g. via a footswitch pedal), or may operate automatically on the basis of a signal detected by the detector. For example, the apparatus may be arranged automatically to switch to the lower power level (e.g. second channel) in the event that the antenna is detected to be in free space (e.g. air). The design of the antenna may be such that reflected signals of large amplitude will be detected when the blade of the antenna is taken out of the tissue and exposed to air. A device for detecting signature events in the reflected signal and which could be used for this purpose is discussed below.

The switch may be a device (e.g. waveguide switch or the like) for switching different physical pathways from a source to the antenna. This embodiment may enable the same source to be used to generate energy e.g. having the same frequency for the treatment channel and the measurement channel. In other embodiments, different frequencies may be used on the two channels, e.g. by having separate frequency sources or using an arrangement of frequency mixers and local oscillators where the local oscillator signals are derived from a single master frequency source. In such embodiments, the switch may comprise a filtering arrangement having two selectable configurations: a first configuration for blocking energy at the frequency of the measurement channel and transmitting energy at the frequency of the treatment channel, and a second configuration for blocking energy at the frequency of the treatment channel and transmitting energy at the frequency of the measurement channel. The filtering arrangement may be implemented using suitable band pass, high pass, band stop, or low pass filters. For example, a band pass filter with a filter profile (pass band frequency range, roll-off characteristic, insertion loss in the pass band, ripple, etc) corresponding to each configuration may be used, which are switchable into a signal pathway that feeds the antenna. In this case each channel may be permanently connected to the signal pathway that feeds the antenna.

The antenna may include a feed structure for connecting to the source and a radiating portion arranged to emit the radiation field. The cutting element may include the radiating portion. The field may thus be emitted whilst simultaneously cutting, thereby providing sealing (cauterising) radiation instantly. The antenna may be arranged to emit the field along the edge of the cutting element. The cutting element may include a coupling portion for receiving energy from the feed structure. The coupling portion may be adapted such that the cutting element receives a substantially maximum field coupling from the feed structure. The cutting element may have a metallized surface except at a proximal coupling portion and a distal radiating portion.

The feed structure may include a waveguide, e.g. loaded with the cutting element.

The antenna may include a plurality of radiating elements, e.g. a plurality of cutting elements attached side by side to increase the length of a cutting blade of the instrument. Alternatively, a plurality of patch antennas may be fabricated on a single cutting element in proximity to the edge. The feed structure may include a power splitter arranged to split power from a single source of microwave radiation evenly between each of the plurality of radiating elements.

The antenna may be incorporated into the cutting blade to form a radiating blade structure. Thus, a sharp edge of the radiating blade may perform the cutting action while the microwave energy may perform the function of coagulating or sealing highly perfused tissue structures as the blade cuts through the tissue to prevent blood loss.

The field profile of the radiated microwave energy may be concentrated at or around the cutting edge of the blade and may be directed into the tissue structure.

As explained in GB 0620060.4, the use of high microwave frequencies (defined here as 10 GHz or higher) offers particular advantage over the use of lower microwave frequency systems due to the limited depth of penetration of the energy by radiation and the ability to enable small sharp blade structures to efficiently radiate energy into the tissue to seal off blood flow by being able to produce uniform fields along the length of the blade whilst at the same time being capable of cutting through the tissue to remove sections of diseased or cancerous tissue. The higher the microwave frequency, the more localised the energy distribution becomes and the energy density at the site where the cutting action takes place is correspondingly high, hence the easier it becomes to effectively seal off blood flow as the cutting blade is introduced into highly perfused biological tissue structures. A further advantage of using microwave energy at a frequency whereby the depth of penetration is small, i.e. less than 5 mm, is that unwanted damage to healthy tissue adjacent to the cutting/coagulating blade can be minimised. A substantially uniform field profile can enable uniform coagulation or other tissue effects along the cutting edge. Substantially uniform in this context means that the field is emitted such that the power delivered is consistent along the cutting edge, e.g. the power density profile along the edge of the blade may vary by about ±20% (or ±1 dB) or less over a majority e.g. ⅔ or more of the blade length.

Using lower frequency microwave energy (e.g. 1 GHz or less) can lead to non-radiating regions of the antenna, which reduces the ability of the device to produce effective coagulation, which may lead to non-effective sealing and partial blood loss. By emitting a uniform field of microwave energy having a suitable energy density along the edge of the blade, the wound is effectively sealed as the surgeon cuts through the tissue structure.

The antenna structures which exhibit the cutting/sealing aspect of the invention disclosed above may also be used for ablating biological tissue, e.g. to enable controlled and focused ablation of cancerous tumours within the liver. This use is enabled by the ability to produce localised or focused microwave energy. In an ablation context, a plurality of radiating elements may be used to spread the energy distribution.

Furthermore, the antenna structures disclosed herein may be used to obtain information concerning the structure of biological tissue e.g. to differentiate between tissue types, and/or to identify various types of cancerous tumours, and/or to determine the stage of tumour growth, and/or to control associated electronic instrumentation to enable the radiating section of the surgical antenna to be impedance matched to the complex impedance of the biological tissue to enable maximum power transfer between an energy source and the biological tissue being treated or resected. This latter feature may be of particular interest during the liver resection process because of the need to efficiently launch energy into liver tissue and blood. These two loads differ in impedance value and so it is desirable to be able to make adjustments in the tuning system to enable the blade and the tissue to always be well matched in terms of impedance. This change in impedance implies that there will be a change in impedance match between the radiating blade and the load, thus a portion of the power will be reflected back along the energy delivery cable and the signals detected at the receiver that relate to the reflected power may be used to enable the necessary adjustments to be made to the variable tuning network.

Selectable Frequencies

In a second aspect, the apparatus may be arranged to deliver microwave radiation at differing frequencies, e.g. to provide different treatment effects. Higher frequencies have a smaller depth of penetration and hence are useful for localised focused treatment, e.g. to cauterise small blood vessels cut by the cutting element. Lower frequencies have a greater depth of penetration, which may be useful for treating larger structures, e.g. to seal or cauterise larger blood vessels. The lower frequency radiation may be activated when necessary, e.g. when a surgeon sees or the system detects a large bleed.

Thus, in one embodiment of the second aspect, a second frequency microwave source and power delivery antenna arrangement may be included in order to cauterise large blood vessels that may not be effectively cauterised using high frequency microwave radiation. The second source may include features of the first aspect described above, e.g. it may be selectively connectable to its antenna via two channels: a first channel responsible for cauterising the large 'bleeders' and a second channel for sensing when it is necessary to activate or deactivate the second energy source.

According to the second aspect of the invention, there may be provided surgical cutting apparatus having: a microwave radiation source arranged to generate a first microwave radiation signal having a first frequency and a second microwave radiation signal having a second frequency; a surgical instrument having a cutting element with an edge for cutting biological tissue, a first antenna connectable to the source to receive the first microwave radiation signal and arranged to emit a substantially uniform microwave radiation field at the first frequency along the edge of the cutting element, and a second antenna connectable to the source to receive the second microwave radiation signal and arranged to emit from the surgical instrument a microwave radiation field at the second frequency, wherein the second frequency is lower than the first frequency.

In this aspect, the surgical instrument may be able to emit a controlled microwave radiation field at two different frequencies. To achieve this, the instrument includes two antennas, which may be adapted to efficiently receive a microwave signal having a certain frequency and to emit a microwave radiation field corresponding to that signal. More than two antennas may be included on the surgical instrument. Alternatively or additionally, the antennas may be arranged to emit a microwave radiation field over different bands of frequencies. If a structure is fabricated that can be operated over a wide bandwidth, i.e. 1 GHz to 18 GHz, only one antenna may be required. An antenna structure may be employed that resonates at two particular frequencies. In particular it may be possible to make use of higher order modes that are set up in waveguide structures to provide energy at the higher frequency. For example, if a rectangular waveguide is used then the dominant mode, the $TE_{10}$ may be employed to deliver energy at the lower microwave frequency, and a higher order mode, the $TE_{31}$, may be used to deliver energy at the higher microwave frequency that is of interest.

Also, if one antenna and feed cable is used to radiate microwave energy at two separate frequencies then it may be desirable to use a signal combining network, or a frequency diplexer, at the generator to enable energy at two different frequencies to be passed (or transmitted) along the delivery cable. In this arrangement, the two energy sources, operating at different frequencies, may be transmitted either separately or simultaneously along the same channel.

The apparatus may include a switch for selectively connecting the first antenna and/or second antenna to the source. The apparatus may be arranged to emit from both antennas simultaneously or from only one antenna at any point in time. In one embodiment, the switch may be arranged to alter signal pathways to the antennas (e.g. where there are separate signal paths from the source), e.g. a waveguide or coaxial switch. In another embodiment, the switch may be arranged to alter filter configurations (e.g. where there is a common signal path carrying energy at both frequencies).

The source may include a first signal generator for producing the first microwave radiation signal and a second signal generator for producing the second microwave radiation signal, the first and second signal generators being connectable to the first and second antennas respectively. The first and second signal generators may be low power oscillators arranged to produce a single stable frequency, e.g. a dielectric resonator oscillator (DRO), voltage controlled oscillator (VCO), Gunn diode oscillator or the like.

The second signal generator may be an apparatus arranged to derive a signal from the first signal generator. For example, the signal produced by the first signal generator may be divided using an appropriate microwave frequency divider, or the signal from the first signal generator may be mixed with a reference oscillator signal using an appropriate microwave frequency mixer to produce the second frequency. An advantage of deriving the second frequency from the first frequency generator is that the two signals are synchronised together. This may offer advantage in terms of system timing control, or by having control of the position of the peaks and troughs in the treatment waveforms produced at the antenna blade. This is particularly useful if the two energy sources are to be operated simultaneously as it avoids having the situation whereby the signal from the first frequency generator interferes with in a destructive manner or cancels the signal from the second frequency generator. This effect can lead to undesirable tissue effects if energy at both the first and second frequency is supplied to the surgical instrument via a common signal path.

As mentioned above, the first and second signal generators may be connectable to the first and second antennas along a common signal path. The signals from the generators may be combined on to the common path using, for example, a microstrip or waveguide signal adder or combiner. The common path may comprise a low-loss coaxial cable capable of propagating a wide range of frequencies, e.g. up to 18 GHz or more. Alternatively, a ridge waveguide which operates over a wide band of suitable frequencies may be used.

The surgical instrument may be connected to the common signal path via a filtering arrangement which ensures that only energy at the first frequency reaches the first antenna and that only energy at the second frequency reaches the second antenna. The filtering arrangement may include two band pass filters, e.g. a first filter to pass energy at the first frequency and reject energy at the second frequency and second filter to pass energy at the second frequency but reject energy at the first frequency). Thus, the first filter may be connectable between the common path and the first antenna and the second filter may be connectable between the common path and the second antenna. For an embodiment having a frequency spacing of around 10 GHz, (e.g. first frequency of 14.5 GHz and second frequency 2.45 GHz) the first and second band pass filters may have a roll off of 40 dB/decade or more, i.e. an unwanted signal that appears at 2 GHz will be attenuated by 40 dB if the band pass filter is designed to pass a 20 GHz signal.

In an alternative arrangement where the two frequencies are well separated in frequency space, e.g. 24 GHz and 500 MHz, the filtering arrangement may comprise a bias 'T' arrangement in which the first filter is an inductor (i.e. circuitry to allow DC or a lower frequency AC signals but not the high frequency signals, e.g. having high inductive reactance $X_L = 2\pi fL$, where f is the frequency and L is the inductance) and the second filter is a capacitor (i.e. circuitry to allow a high frequency signal to pass but not DC or lower frequency signals, e.g. having high capacitive reactance $$X_C = \frac{1}{2\pi fC},$$

where f is the frequency and C is the capacitance).

The first and second signal generators may be connectable to the first and second antennas along separate signal paths. The signal paths may be provided in media which permit propagation of the microwave radiation. The media may comprise a waveguide, a coaxial cable or the like. A separate transmitting medium may be provided for the first and second frequencies. Each transmitting medium may be adapted to transmit efficiently signals at the respective frequency. The transmitting media may be flexible to aid manipulation of the surgical instrument.

The apparatus may include a reflected radiation detector arranged to receive signals reflected back from each antenna, and an impedance adjustor connected between the source and each antenna, wherein the detector is arranged to detect the magnitude and phase of the reflected signal and the impedance adjustor has an adjustable complex impedance that is controllable based on the detected magnitude and phase.

The apparatus may therefore be arranged to match the impedance of the apparatus seen at the load (tissue) through either the first or the second antenna to the impedance of the load (tissue) itself to enable efficient power transfer. The impedance matching may be dynamic, e.g. adjustment may occur automatically in real time.

The first and second aspects of the invention may be combined. Thus, each antenna may be selectively connectable to the source via a first channel for conveying its microwave signal at a first power level for treatment and a second channel for conveying its microwave signal at a second power level for measurement, and wherein each antenna is connected to the detector via a signal transfer unit which is arranged to route signals reflected from the antenna along the second channel directly to the detector. In this way, information can be obtained to decide whether or not to activate each of the antennas. The second antenna may emit a signal at the second (lower) power level whilst the first antenna is emitting at the first (higher) power level. Reflected signals from the second antenna at the second power level may be used to decide whether to switch the second antenna to the first power level.

Any of the features described with respect to the first aspect may also be applicable to the second aspect. For example, the first power level may be two or more orders of magnitude greater than the second power level.

Each antenna may include a feed structure connectable to the source (e.g. via a dedicated or common signal path) and a radiating portion arranged to emit its microwave radiation field. For example, the cutting element may provide the radiating portion of the first antenna, and may include a coupling portion for receiving energy from the feed structure (e.g. waveguide) of the first antenna. The coupling portion may be adapted such that the cutting element receives a substantially maximum field coupling from the feed structure of the first antenna. The cutting element may have a metallized surface except at the coupling portion and the radiating portion of the first antenna. The first antenna may be arranged to emit its microwave radiation field along the edge of the cutting element. Thus, the radiating portion may be the edge of the cutting element, whereby the surgical instrument provides a radiating blade structure.

The second antenna may also be arranged to emit its microwave radiation field along the edge of the cutting instrument. The second antenna may be a self contained structure e.g. mounted on the cutting element. For example, the second antenna may be a monopole, a loop, a patch, or a dipole antenna attached to the cutting element, e.g. adjacent the edge of the cutting element. Alternatively, the second antenna may comprise a plurality of radiating elements, e.g. a plurality of patch antennas fabricated on the cutting element in proximity to its edge. The fields emitted by each patch may complement one another to produce an overall field that is substantially uniform across a target region. The target region for the second antenna may be localised around the edge of the cutting element. It may extend further away from the cutting element than the field emitted by the first antenna. The feed structure of the second antenna may include a power splitter arranged to split power from the source evenly between each of the plurality of radiating elements.

The first frequency may be in the range 10 to 40 GHz and the second frequency may be in the range 100 MHz to 5 GHz.

The second aspect of the invention may also be expressed as a surgical instrument having a cutting element with an edge for cutting biological tissue, a first antenna arranged to emit a substantially uniform microwave field of radiation at a first frequency at the edge of the cutting element, and a second antenna arranged to emit a microwave radiation field at a second frequency from the cutting element, the second frequency being lower than the first frequency.

The first antenna may be integral with the cutting element and the second antenna may be mounted on the cutting element. Thus, the cutting element may be arranged to receive directly (e.g. from a waveguide) the microwave radiation at the first frequency. The cutting element may comprise a ceramic body having a coupling portion for attaching to a waveguide and a blade portion which includes the edge for cutting biological tissue. The cutting element may have a metallized surface except at the coupling portion and blade portion such that the cutting element radiates microwave energy received at the coupling portion from the blade portion. The dimensions of the ceramic body may be selected based on the first frequency to ensure a substantially uniform field is emitted from the blade portion. In order to ensure that a good impedance match exists between the sapphire (or alumina) radiating blade (that may be a peculiar shape) and the rectangular waveguide cavity, an impedance transformer may be used. This can take account of the fact that the blade and the waveguide cavity are different in terms of size and contain different dielectric materials and permit efficient power transfer therebetween. The choice of transformer depends largely on the bandwidth requirement, and the size and weight constraints placed on the product or device. A tapered transformer may be used in wide bandwidth applications, but these structures tend to be relatively long, i.e. they normally consist of a plurality of quarter wavelength impedance transforming sections. An alternative structure is the step design; these allow relatively narrow bandwidth operation, but can be physically realised using short sections of material. In between the two designs are the multiple step designs, where any increase in bandwidth is paid for by an increase in complexity and size. This structure may be preferred in an embodiment of the invention. Due to the fact that the bandwidth requirement for the surgical resection tool is low, i.e. less than 50 MHz, and the device is required to be small and lightweight for ease of manipulation by the surgeon, a two step design was considered to provide the optimal solution. The slightly wider bandwidth offered by the use of two steps allows for manufacturing tolerances in the transformer or other components and slight variations in the frequency of the source to be taken into account. In a two step transformer, the change in parameters is achieved in two steps, separated by approximately an odd number of quarter wavelengths at the frequency of interest.

The first antenna may be arranged to radiate microwave radiation from the edge of the cutting element. The second antenna may be mounted on the cutting element, e.g. mounted on the first antenna. The second antenna may include a radiating portion mounted at the edge of the cutting element. A feed portion may also be mounted on the cutting element to deliver microwave radiation to the radiating portion. The feed portion may be a coaxial cable, e.g. attached to the bottom of the cutting element. The radiating portion may include a microstrip antenna, e.g. fabricated on a dielectric layer formed on the layer of metallization adjacent to the (non-metallized) blade portion.

Variable Treatment Frequency

In a third aspect, the apparatus is arranged to emit a plurality of selectable frequencies from the same antenna. For example, the apparatus may emit over a band of frequencies or be arranged to emit efficiently at a plurality of discrete frequencies. In this aspect, the source may be arranged to generate an output whose frequency can be selected, e.g. adjusted. For example, the source may be a wideband energy source capable of generating a range of frequencies to enable ablation of a range of tissue structures. As explained above, higher microwave frequencies may be suitable to cauterise or seal fine structures or small blood vessels and lower microwave frequencies may be suitable to cauterise or seal larger tissue structures or large blood vessels. In this instance, it may be preferable to design the impedance matching transformer that matches the waveguide cavity to the blade using a tapered structure rather than a step structure, or to use a step structure with at least three steps, in order to increase the bandwidth of operation.

According to the third aspect of the invention, there may be provided surgical cutting apparatus having: a microwave radiation source arranged to generate a microwave radiation signal having a stable output frequency; and a surgical instrument having a cutting element with an edge for cutting biological tissue, and an antenna connected to the source to receive the microwave radiation signal and arranged to emit a substantially uniform microwave radiation field corresponding to the microwave radiation signal from the edge of the cutting element, wherein the output frequency is adjustable. Thus, the stable output frequency may be selectable from a range of frequencies that can be generated by the source. The source may include a wideband frequency oscillator for producing an input over a selectable range of frequencies. The output frequency may be selected for a certain condition e.g. tissue type at the antenna. For example, the output frequency may be selected to set up a resonant condition when the antenna is in contact with the tissue. Alternatively, the output frequency may be selected to correspond to a frequency where an energy absorption peak occurs in the biological tissue being treated.

The source may comprise a variable frequency signal generator. The variable frequency generator may comprise a voltage controlled oscillator (VCO), wherein the output frequency is set by varying the voltage on a varactor diode, which in turn varies the capacitance of an L-C resonant circuit. For example, the HMC5343LP4 (E) from Hittite Microwave Corporation can produce a range of frequencies between 23.8 GHz and 24.8 GHz using the arrangement above when the tuning voltage is varied between 0 V and 10 V.

Alternatively, the variable frequency generator may comprise a frequency synthesiser which is arranged to generate energy over a range of frequencies from a fixed frequency source. A frequency synthesiser can be used to generate a stable and precise output signal on any one of a number of preset or programmable frequencies.

The variable frequency signal generator may be arranged to output a first signal having a stable frequency within a range of frequencies and an amplification unit arranged to amplify the first signal into a second signal having a power level suitable for treatment, wherein the amplification unit is capable of amplifying a signal having any frequency in the range of frequencies to a power lever of 10 W or more. In other words, the amplification unit is operable over a range of frequencies generated by the signal generator. The range of frequencies may correspond to those conveyed by a standard waveguide. Alternatively, to achieve a greater bandwidth without substantially increasing the risk of moding, the signal generated by the source may be conveyed to the amplification unit and then the antenna by a coaxial cable. Coaxial cable can exhibit low losses within relative wide frequency ranges. For example, the range of frequencies may be 100 MHz to 18 GHz. So long as the outer diameter of the co-axial cable is not comparable to or greater than a half the wavelength at the highest microwave frequency that may be of interest then a transverse electromagnetic (TEM) wave will propagate. Non standard waveguide structures may also be considered, for example, ridge waveguide structures are preferred since they are known to enable microwave energy to propagate over a much wider band of frequencies than that possible using standard rectangular or cylindrical waveguide structures. In this case, the amplification unit may include a travelling wave tube (TWT). In one embodiment, the amplification unit may be capable of amplifying a signal having any frequency in the range of frequencies to a power level of 100 W or more.

As mentioned above, the frequency may be adjustable depending on a particular condition (e.g. tissue load or absorption peak) at the edge of the antenna. The apparatus may detect that condition. For example, the apparatus may include a reflected radiation coupler and detector arranged to receive signals reflected back from the antenna, wherein the detector is arranged to detect the magnitude and phase of the reflected signal whereby the adjustable frequency of the source is controllable based on the detected magnitude and phase.

In one embodiment, the source may be arranged to sweep the output frequency of a forward microwave radiation signal across a range of frequencies, whereby a suitable frequency for treatment is selectable from the range of frequencies based on the detected magnitude and phase of reflected signals corresponding to the swept forward signal. With this arrangement the most suitable treatment frequency for a particular antenna configuration in a particular tissue type can be found. For example, a certain antenna shape may radiate more effectively at certain specific frequencies ('sweet spots'). The sweet spots can be found by sweeping the frequency of the forward signal and monitoring the reflected signal received back from the antenna for the swept frequencies. A small reflected signal may indicate a sweet spot, i.e. a frequency where power is delivered efficiently into the tissue. A null or minimum signal detector may be implemented in hardware using discrete analogue circuit components, such as operational amplifiers and comparators, or a software solution may be implemented whereby the analogue signal is digitised using an analogue to digital converter and the digital version is processed using a microprocessor or a DSP unit.

The features of the first and third aspects may be combined. Thus, the antenna may be selectively connectable to the source via a first channel for conveying the microwave signal at a first power level for treatment and a second channel for conveying the microwave signal at a second power level for measurement, and wherein the antenna is connected to the detector via a signal transfer unit which is arranged to route signals reflected from the antenna along the second channel directly to the detector. The frequency may be swept on the second channel to minimise the risk of tissue and/or instrument damage. When the desired frequency is determined, the apparatus may be switched to the first channel. The first power level may be two or more orders of magnitude greater than the second power level.

The structure of the antenna itself may include any of the features discussed above in relation to the first or second aspects of the invention. Field simulation modelling may be carried out on different antenna shapes to investigate and determine theoretical values for the preferred emitted frequency. The antenna may therefore be configured to emit efficiently within the range of frequencies of the source. The adjustable source provides the additional advantage of 'fine tuning' the frequency to adjust for any differences between the theoretical best frequency value for a particular antenna and the best frequency value in practice.

Power Level Boost

In a fourth aspect, the invention may permit a treatment level of microwave power delivered via the cutting element to be manually boosted. One advantage of this is to enable the system to deal effectively with large blood vessels. In one arrangement, the system described in UK patent application no. 0620060.4 may be modified to enable a user of the apparatus (e.g. surgeon) to operate a switch (e.g. footswitch pedal or push button) to provide a boost of power into the tissue. Higher power levels at the same frequency may be required when large blood vessels are encountered. Using the higher power level may reduce the time it takes to seal large open blood vessels.

According to the fourth aspect of the invention, there may be provided surgical cutting apparatus having: a microwave radiation source arranged to generate microwave radiation; a surgical instrument having a cutting element with an edge for cutting biological tissue, and an antenna connected to the source and arranged to emit a substantially uniform microwave radiation field at the edge of the cutting element; and an amplification unit between the source and the antenna for amplifying the microwave radiation signal generated by the source, wherein the amplification unit is manually switchable between a first configuration for amplifying the signal to a first power level and a second configuration for amplifying the signal to a second power level that is higher than the first power level.

Typical treatment power levels (i.e. the first power level) may be in the range 10 to 120 W. The boosted power level (i.e. the second power level) may increase the first level by 20 to 50 W or more. For example, the boosted power level may be more than 120 W, e.g. in the range 120 to 300 W or more. The amount of boost available may be limited by the maximum power handling capability of the components used within the system, for example, the reflected power protection circulators and associated power dump loads, and the material used to implement the radiating blade. In particular, it is desirable to avoid overstressing the blade material by allowing the power to be too high for too long a time duration. Power P dissipated in the material per unit volume is given by: $P=2\pi\in_0\in"E_{rms}^2$, where $\in"$ is the loss factor and $E_{rms}^2$ is the electric field strength.

A manually operable switch for providing the power boost may be provided in addition to a switch for activating normal operation of the apparatus. For example, the switches may be suitably marked e.g. differently coloured footswitch pedals. The use of two footswitch pedals is already known for existing (radio frequency) electrosurgical procedures involving cut and coagulation operations, e.g. to produce a high voltage waveform and a high current respectively, so the apparatus is compatible with existing surgical techniques.

The amplification unit may include an amplifier and a feed unit arranged to receive the microwave radiation signal from the source and to generate a drive signal for driving the amplifier, wherein the feed unit is arranged to generate a drive signal in the second configuration that has a higher power level than a drive signal in the first configuration. Thus, the power boost may be implemented by increasing the power level input to an amplifier. The feed unit may be arranged to drive the amplifier into saturation in the second configuration. Alternatively, the feed unit may be arranged to drive the amplifier to produce a maximum predetermined power at an output port thereof in the second configuration. For example, it may be desirable to set a upper limit to the amount of power produced by the apparatus to avoid unnecessary tissue damage. This may be achieved by controlling the drive signal provided to the amplifier. Alternatively, the power may be ramped from the level used for normal operation to a maximum (saturated) power level that can be delivered by the particular amplifier arrangement used in the system.

The feed unit may include a first signal path for conveying the microwave radiation signal between the source and amplifier in the first configuration and a second signal path for conveying the microwave radiation signal between the source and amplifier in the second configuration, the first and second signal paths being manually selectable to switch the amplification unit between the first and second configurations. Separate signal paths may be advantageous in that components in the line-up on a 'normal' treatment signal path (at the first power level) can be bypassed in a boosted treatment signal path to enable the higher power level to be transmitted efficiently, i.e. to reduce or minimise losses on the signal path between source and antenna.

The source may be connected to the feed unit by an input switch which is operable to direct the microwave radiation signal to the first or second signal path. Alternatively or additionally, the feed unit is connected to the amplifier by an output switch which is operable to direct a drive signal from either the first or the second signal path to the amplifier.

An actuator may be arranged to simultaneously operate the input and output switches to select either the first or second signal path. The actuator may be a footswitch pedal, as mentioned above.

The second signal path may include a boost amplifier e.g. a preamplifier to increase the power level of the drive signal in the second configuration.

The apparatus may include a reflected radiation detector arranged to receive signals reflected back from the antenna and an impedance adjustor on the first signal path, wherein the detector is arranged to detect the magnitude and phase of the reflected signal and the impedance adjustor has an adjustable complex impedance that is controllable based on the detected magnitude and phase of the measured signals. Using this arrangement it may be possible to implement an automatic control system capable of sensing high perfusion during 'normal' resection operation (at the first power level), whereby the apparatus can automatically switch to the second power level. The condition that may be used to indicate that a large uncontrollable bleed has occurred may be indicated by a constant voltage level detected by the reflected power measurement signal, where the constant voltage level is representative of a well matched condition, i.e. a low signal level from the reflected power monitor/detector, for a longer than average time duration or time slot. This may be an effective means of establishing this condition due to the fact that in normal operation it is to be expected that there will be a regular change in reflected signal due to the continuous change in impedance as the blood rich condition is rapidly changed to the coagulated condition as the blade is moved along or through the tissue. Voltage levels and time slots for different conditions may be discovered by experimentation and clinical trials, and the system may be arranged to enable a variety of time slots and levels to be set up.

The second signal path may bypass the impedance adjustor (i.e. the power controlling unit in 'normal' operation). When operating on the second signal path, the apparatus may therefore be arranged to overdrive the amplifier (or drive it into saturation). The second signal path may be utilised for a short period of time e.g. 5-10 seconds or less to enable the high perfusion (e.g. due to a large open blood vessel) to be treated.

The fourth aspect may be combined with the first aspect. In such a case there are effectively three power levels: a low power level for measurement, and two high power levels for normal treatment and boosted treatment respectively. Thus, the antenna may be selectively connectable to the source via a first channel which includes the amplification unit for providing a microwave signal at the first or second power level for treatment and a second channel which bypasses the amplification unit for conveying a microwave signal at a lower power level for measurement, wherein the antenna is connected to the detector via a signal transfer unit which is arranged to route signals reflected from the antenna along the second channel directly to the detector.

As disclosed above, the signal transfer unit may include a circulator connected between the source, the antenna and the detector on the second channel, the circulator being arranged to direct a forward signal from the source to the antenna and a reflected signal from the antenna to the detector.

The apparatus may include a switch arranged to permit selection of the first or second channel. The channel switch may be separate from a switch arranged to permit selection of the first or second power level.

The fourth aspect may also be combined with any other features of the first, second or third aspects mentioned above. In particular, when combined with the second embodiment, the boost arrangement may be provided for both the first and second frequencies. The second (lower) frequency is already selected to cope with large blood vessels. Providing the boost capability may provide a back up for addressing extreme conditions, e.g. very large bleeds.

Event Monitor

In a fifth aspect, the invention may provide a reflected power monitor arranged to recognise certain behaviour in a reflected signal received back from the antenna and enable action to be taken automatically in response to the recognised behaviour. The behaviour in the signal may be indicative of a condition in the tissue being treated. For example, the signal may indicate that the impedance of the tissue is not changing, which may mean that the power delivered is insufficient for effective treatment. The power level may be increased (e.g. using the boost idea of the fourth aspect) automatically or manually in response to this recognised behaviour. In another example, this arrangement can be used to reduce or prevent the phenomenon or tissue 'spitting' that can occur during treatment. Tissue 'spitting' or 'popping' is thought to be caused by pressure building up where a energy emitting surgical instrument (e.g. probe or blade) is inserted into tissue. The combination of pressure and energy from the instrument can cause small bits of tissue to be removed from the treatment site and, in some cases, fly over a range of up to or in excess of 1 m. It is highly desirable to avoid blood or e.g. liver tissue (especially diseased) being spat out on to surgeon or other staff during the operation of the present apparatus. This effect may also be described as a cavitational effect.

This effect may cause a problem in a resection procedure if the radiating blade is held in one position for a few seconds or maybe even less. The effect may occur particularly when it is necessary to tackle (i.e. seal or cauterise) a large bleeder (open blood vessel) during operation. Due to the small blade structures and high localised power levels that may occur with the apparatus discussed herein, the power density along the blade can be very high, especially if a boost in power is provided when a large bleed from a large blood vessel is encountered.

The inventors have discovered that the behaviour of the reflected power can indicate in advance when a spit event is about to occur. Moreover, the inventors have discovered that it is possible to prevent the spit event from occurring if suitable action is taken in response to the relevant behaviour.

According to the fifth aspect, there may be provided surgical cutting apparatus having: a microwave radiation source arranged to generate a microwave radiation signal; a surgical instrument having a cutting element with an edge for cutting biological tissue, and an antenna connected to the source and arranged to emit a substantially uniform microwave radiation field at the edge of the cutting element; a reflected radiation detector connected between the source and the antenna to detect signals reflected back from the antenna; a reflected power monitor arranged to detect a signature event in the reflected signals detected by the reflected radiation detector; and a power level adjuster connected between the source and antenna and arranged to automatically adjust a power level of the microwave radiation signal received by the antenna if the monitor detects a signature event.

The signature event may be any detectable behaviour in the reflected signal. For example, it may be a certain rate of change of reflected power or a constant level of reflected power for a certain time slot or duration. The signature event may be derived from behaviour in the reflected power, e.g. the reflected power may be used to determine changes in the impedance of the tissue; these changes may indicate the signature event. In one embodiment, this arrangement can be used to ensure that the radiating blade cannot cause excessive collateral damage to the tissue if it is held in a particular position for a period of time that is greater than that required to effectively cut the tissue and coagulate the bleed. If the arrangement detects an event indicating that the blade is held in one place for too long (e.g. a constant voltage indicative of a well matched condition is detected) then the power can be reduced to reduce or prevent collateral damage.

The reflected power monitor may be arranged to detect a rapid voltage spike in the reflected signal. For example, the monitor may include a differentiator arranged to measure a value of dv/dt (change of voltage with time) for the reflected signals. The differentiator may be arranged to compare the measured value to a threshold value, whereby the signature event is a value of dv/dt that is higher than a threshold. This arrangement may be used to detect tissue 'spitting', which the inventors have found is preceded by a voltage spike with a sharp rise or fall. The apparatus may continuously monitor the reflected power during treatment and if the signature event (value of dv/dt above the threshold) is detected, the power level may be arranged to immediately reduce the power level from a first value to a second value. Thus, the apparatus may back off (or reduce) the power level as soon as the signature (signal) that is known to lead to a 'spit' is observed. The first value of the power level may be one or more orders of magnitude greater than the second value of the power level. In one embodiment the first (treatment) power level is 100 W or more and the second power level is 10 W or less.

The differentiator (e.g. slope detector differentiator) may be implemented in an analogue manner, i.e. using discrete operational amplifiers, signal comparators, an arrangement of capacitors and resistors and MOSFET switches, or using digital components, e.g. a computer or a DSP unit.

The threshold may be adjustable e.g. to enable a sensitivity to tissue spitting to be selected.

The power level adjuster may be arranged to ramp the power level back to the first value in a recovery time period after the reduction in power level. In practice, the power may need to be ramped back up relatively rapidly to permit treatment to continue without substantial instrument downtime or to ensure that the overall patient treatment time is not excessive. For usage in tumour ablation, it must be ensured that critical temperatures within the tissue are reached in order to ensure that all of the cancerous tissue/cells has/have been totally destroyed. The recovery time period may therefore be 100 ms or less.

The reflected radiation detector may be selected to be sensitive to the changes in the reflected signal which represent the monitored behaviour. Thus, if a diode detector is used e.g. connected to a coupled port of a directional coupler connected between the source and the antenna, then its rise/fall time may be selected to capture the signature event. For example, the detector may be a diode detector having a rise/fall time of 1 μs or less to capture the voltage spike associated with tissue spitting event that may exhibit a rise/fall time of 10 ms. In one embodiment, a tunnel diode based detector with a very fast pulse response may be used, e.g. product number ACTP1505N from Advanced Control Systems.

The power level adjuster may comprise an impedance adjustor connected between the source and the antenna. The impedance adjustor may also be used in an impedance matching arrangement, wherein the detector may be arranged to detect the magnitude and phase of the reflected signal and the impedance adjustor may have an adjustable complex impedance that is controllable based on the detected magnitude and phase. In this arrangement the impedance adjustor may therefore be arranged to match the impedance of the apparatus to the impedance of the load (tissue) to enable efficient power transfer. The impedance matching may be dynamic, e.g. adjustment may occur automatically in real time. When a signature event is detected by the monitor, the impedance matching may be overridden by the response to that signature event.

The reflected power monitor may also be arranged to provide user information e.g. to guide the surgeon during a surgical resection procedure. The fifth aspect may alternatively be expressed as surgical cutting apparatus having: a microwave radiation source arranged to generate a microwave radiation signal; a surgical instrument having a cutting element with an edge for cutting biological tissue, and an antenna connected to the source and arranged to emit a substantially uniform microwave radiation field at the edge of the cutting element; a reflected radiation detector connected between the source and the antenna to detect signals reflected back from the antenna; and a reflected power monitor arranged to detect a signature event in the reflected signals detected by the reflected radiation detector; wherein the monitor is arranged to emit an audible or visual signal when a signature event is detected. The audible or visual signal may be representative of the detected event. Thus, a certain audible signal may provide information to the surgeon to ensure that he/she moves the blade in an optimal manner. The audible signal may be any of a range of sounds or a digitally synthesised voice. This feature can be used to reduce or minimise collateral damage caused to healthy tissue during the procedure as it could avoid the surgeon leaving the blade in contact with the tissue for longer periods of time than is necessary.

The fifth aspect may be combined with any feature or combination of features of the first, second, third or fourth aspects described above.

The five aspects discussed above may be used with any of the surgical instruments disclosed in UK patent application no. 0620060.4. In general, the surgical instrument comprises a body, e.g. of a dielectric material, which is formed into a cutting element, e.g. having a blade with an edge for cutting tissue. Various blade shapes may be used, e.g. a 'tooth' shape blade, a scalpel shape blade, a 'paint stripper' shape blade, a chisel shape blade, a hemispherical shape blade, a kitchen knife shape blade and a carving knife shape blade. In the instance where a 'tooth' shape blade is used, it may be preferable for the tooth to take the form of a triangular structure with a 60° angle at each of the base corners to provide the ability to dig into the tissue. The surgical instrument may be disposable.

An antenna is either integrally formed with or fabricated on to the body of the surgical instrument. Using appropriate electromagnetic field simulation modelling tools, the configuration of the antenna can be arranged to cause the field emitted by the antenna to be concentrated in a substantially uniform manner at the edge of the blade.

One embodiment of the surgical instrument is a loaded waveguide antenna, which uses a sapphire material to form a blade which acts as both a microwave field radiating structure and as a sharp cutting tool. The shape of the sapphire section inside the waveguide (the impedance transformer) and the design of the end section or blade housing may be designed e.g. using electromagnetic field simulations tools to provide a good impedance match between the biological tissue, the sapphire blade and the waveguide cavity. The sapphire material may be partially metallized over its surface using an electroforming process with only the end of the blade exposed. A viable alternative to using sapphire for implementation of the radiating/cutting blade and the impedance transformer is Alumina. Alumina is a good engineering material that is regularly used in the development of low loss microwave components and has similar microwave properties to sapphire. Alumina is composed of a large volume fraction of small sapphire crystals bonded together with a small quantity of glass. The proportion of sapphire determines the quality of the alumina. Table 1 may be used to compare the electrical properties of 96% and 99.5% pure Alumina with sapphire.

TABLE 1

Comparison of properties of viable materials for the integrated Transformer and blade

| Material | Relative Dielectric Constant ($\in_r$) | Loss tangent (tan δ) |
| --- | --- | --- |
| 96% Pure Alumina | 9.3996 | 0.0004 |
| 99.5% Pure Alumina | 9.9 | 0.0001 |
| Sapphire | 11.5 | 0.00003 |

The exposed section is the radiating structure. The step transformer made from sapphire (or alumina) material provides an impedance match between the impedance of an unloaded waveguide section, which is a high impedance close to that of air, i.e. 377Ω (it may be noted that it is normal for an open section of waveguide to give a return loss of −10 dB when exposed to air) and the biological tissue, which may be a low impedance, for example, between 100Ω and 1Ω. The size of the waveguide depends on the frequency of operation. For example, a section of WG18 (WR62) flexible waveguide can be used to operate over the frequency range of between 12.4 GHz and 18 GHz. This is a suitable structure to use at one of the spot frequencies of operation discussed herein, 14.5 GHz. Other waveguides operate over different frequency ranges.

BRIEF DESCRIPTION OF THE DRAWINGS

Embodiments of the aspects outlined above are described in detail below with reference to the accompanying drawings, in which:

FIG. 4 is a side view of a surgical instrument having a blade and two antennas, and is an embodiment of the second aspect of the invention;

FIG. 5 is a partial cross-sectional side view of another surgical instrument having a blade and two antennas, and is another embodiment of the second aspect of the invention;

DETAILED DESCRIPTION

Further Options and Preferences

Selectable Channels

Figure 1:
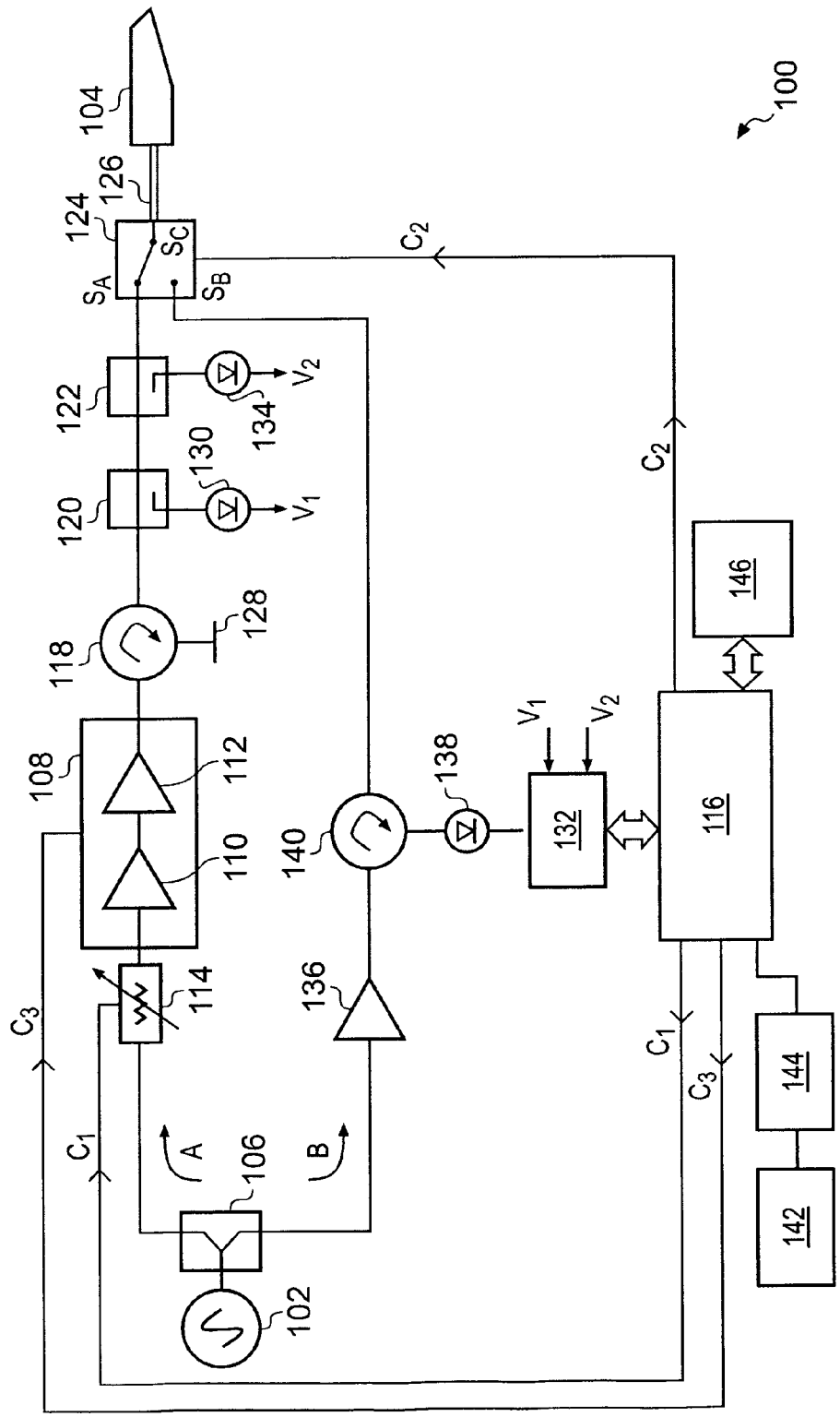
FIG. 1 is a schematic system diagram showing components of surgical cutting apparatus with a treatment channel and a measurement channel for radiation from a source, and is an embodiment of the first aspect of the invention.

FIG. 1 shows surgical cutting apparatus 100 e.g. suitable for use in surgical resection procedures (e.g. liver resection) which is an embodiment of the first aspect of the invention. Many of the individual components are similar to those used in the apparatus disclosed in UK patent application 0620060.4. A main difference is the provision of a splitter 106 which separates the output of the source 102 into two channels A, B for conveying microwave radiation from a source 102 to an antenna (not shown) on surgical instrument 104. The channels deliver radiation to the surgical instrument at different power levels. In this aspect, there is a treatment channel A for delivering radiation at a power level which will seal or cauterise blood vessels that are cut open by the blade and a measurement (or sensing) channel B for delivering radiation at a lower power level which will not substantially affect tissue at the blade but which can be used to obtain information about that tissue.

In detail, FIG. 1 shows a source 102 (e.g. an oscillator source such as a VCO or DRO) which outputs a low power signal (e.g. between 0 dBm and 10 dBm) having a stable frequency. The frequency may be any suitable frequency above 10 GHz. For example the frequency may be 14.5 GHz, 24 GHz or more.

The output from the source 102 is split into two parts by power splitter 106, which may be a −3 dB coupler, a 3 dB power splitter, or a directional coupler. The device may be realised in a waveguide, microstrip, or co-axial arrangement. One part is directed along treatment channel A and the other part along measurement channel B.

On treatment channel A, the signal drives the input to power amplifier unit 108, which in this embodiment comprises a preamplifier 110 and a power amplifier 112. The amplifiers 110, 112 may be any of a travelling wave tube (TWT), a magnetron, a Klystron, a semiconductor amplifier or the like that is able to generate power levels of between 1 W and 500 W at frequencies in the range of between 10 GHz and 40 GHz. In this embodiment, the amplifiers may have a gain of 20 or more, e.g. 20 and 30 respectively. A microwave power module, e.g. comprising a series combination of a solid state driver amplifier and mini-TWT, may be used in the power amplifier unit 108. It may be desirable to combine a plurality of microwave power modules using a low loss waveguide or microstrip power combiner to produce the desired power level. The configuration of the power amplifier unit 108 is determined by a control signal $C_3$ provided by microprocessor/DSP unit 116.

An adjustable signal attenuator 114 is located on the treatment channel A between the splitter 106 and the amplifier unit 108. The function of the attenuator 114 is to reduce the amplitude of the signal from the splitter 106 to enable the output power produced by the amplifier unit 108 to be controlled. The attenuator 114 is adjustable according to a control signal $C_1$ from a microprocessor/DSP unit 116, which is discussed below. The attenuator 114 may be a PIN diode attenuator, and is preferably arranged to provide a range of attenuation which enables the amplifier unit 108 to be driven into saturation when the attenuation level is a minimum value and the power to be backed off sufficiently when the attenuation is set to a maximum value, i.e. a level may be set whereby the system enables cauterisation or coagulation to occur in not such highly perfused tissue, or where the power level does not cause the blood to coagulate. In the former case, this high level of control enables coagulation to occur without causing unnecessary collateral damage, or damage to healthy tissue structures adjacent to the cut.

The output from the power amplifier unit 108 is fed into the input (first) port of a microwave circulator 118 whose function is to protect the amplifier unit 108 against high levels of reflected power being returned to the output stage of the amplifier unit, which may cause damage to the amplifier unit, or cause the amplifier to behave like an oscillator due to the impedance mismatch seen at the output stage. The circulator 118 operates to allow power flow in a clockwise direction only. The power from the output of amplifier unit 108 is thus diverted to the second port of power circulator 118 where it is directed towards the surgical instrument 104 via directional couplers 120, 122, waveguide switch 124 and transmission cable 126. The third port of the circulator 118 is connected to a power dump load 128 whose function is to absorb reflected power returned back along transmission cable 126 that may enter the second port of power circulator 118. Any reflected power received into the second port is diverted to the third port and into the power dump load 128. The impedance as seen at the third port of circulator 118 is arranged to be the same as that as seen at the input to the dump load 128. This ensures that there is no power returned back to the first port of power circulator 118. In practice, the third port of circulator 118 is well matched with the input impedance of the dump load and a negligible amount of power is transferred or transported from port three to port one of circulator 118. It is normal practice for the impedance of the dump load to be 50Ω.

The output power from the second port of the circulator 118 is fed into the input to forward power directional coupler 120, which is configured to measure the forward power by sampling a portion, i.e. 10% or 1%, of the forward going power. The coupled port of forward directional coupler 120 is connected to a detector 130 which converts the microwave power sampled by the coupler 120 into a DC level or lower frequency AC level. The detector 130 may include any suitable diode, e.g. a zener diode, a zero bias Schottky diode, or a tunnel diode. Alternatively, a homo/heterodyne detection unit may be employed in the place of the detector 130. In the latter embodiment, both phase and magnitude can be measured.

The output $V_1$ from detector 130 is fed into an analogue to digital converter 132 where it is converted into a digital signal so that it can be manipulated or used by microprocessor/DSP unit 116.

The output power from forward power directional coupler 120 is fed into the input port of reverse power directional coupler 122, which is configured to measure the reflected power by sampling a portion of the power returned along cable 126 due to a mismatch between the distal end of surgical instrument 104 and biological tissue, i.e. the reflection coefficient is either greater than or more negative than zero, e.g.

0.5 or −0.5, but is within the bounds of −1 to +1. The actual value is dependent upon whether the load impedance is greater or less than the characteristic impedance of the cable and blade/transformer assembly. The coupled port of reverse power directional coupler 122 is connected to a detector 134 which converts the microwave power sampled by the backward directional coupler 122 into a DC level (or lower frequency AC signal). The detector 134 may be a diode detector which includes any suitable diode, e.g. a zener diode, a zero bias Schottky diode, or a tunnel diode. Alternatively, a homo/heterodyne detection unit may be employed in the place of the detector 134. The output $V_2$ from detector 134 is fed into the analogue to digital converter 132 where it is converted into a digital signal so that it can be manipulated or used by microprocessor/DSP unit 116. The value of the detected signal is used to determine any action that will (or needs to be taken by the system, i.e. it may be necessary to increase the output power from the amplifier to compensate for any impedance mismatch between the blade and the tissue.

The output power from reverse power directional coupler 122 is connected to a first port $S_A$ of a waveguide switch 124. The waveguide switch 124 is arranged to connect either the (high power) treatment channel A or the (low power) measurement channel B to the cable 126 which feeds surgical instrument 104. In FIG. 1, the treatment channel is selected, i.e. first port $S_A$ is connected to output port $S_C$. In this embodiment, the waveguide switch 124 is a single-pole-two-throw (SP2T) switch, where the first port $S_A$ and second port $S_B$ are selectively connectable to the output port $S_C$. The common contact (output port $S_C$) is connected to cable 126. Other switch types may be used, e.g. a coaxial switch or a high power PIN/varactor switch.

The configuration of the waveguide switch 124 (i.e. position of movable waveguide section within waveguide switch 124 to provide connection path $S_A \rightarrow S_C$ or $S_B \rightarrow S_C$) is determined by a control signal $C_2$ provided by microprocessor/DSP unit 116.

In this embodiment the transmission cable 126 is a flexible/twistable waveguide assembly, but a low loss coaxial cable assembly may be used instead. It is preferable to cover the flexible/twistable waveguide with a rubber jacket, i.e. a neoprene rubber may be used.

The surgical instrument 104 comprises a blade structure which has the basic form of a scalpel, where two sharp angled cutting edges are machined at one end of a rectangular block of material, e.g. alumina, sapphire or the like. The sides of the rectangular block (i.e. the side surfaces and top and bottom surfaces) are metallized. However, the faces which meet at the cutting edges are not metallized; the alumina is exposed at this position to form a radiating portion.

The dimensions for the blade structure may be obtained based on information about the overall structure and configuration (e.g. wavelength of operation) of the surgical instrument, e.g. by performing microwave field simulations.

In the low power measurement or detection mode, the second port $S_B$ of waveguide switch 124 is connected to the output port $S_C$ to enable the (low power) measurement signal from measurement channel B to be transmitted to the distal radiating tip of surgical instrument 104.

On measurement channel B, the signal from source 102 is input to a low noise, low power amplifier 136. In some embodiments low power amplifier 136 may be omitted because the signal generated by source 102 and split by splitter 106 has a high enough power such that a portion of the transmitted signal that is reflected at the distal end of surgical instrument 104 has an amplitude that is high enough to be detectable by a reflected power detector 138. The reflected power detector may be a magnitude detector, e.g. a diode detector as shown or any other suitable magnitude detector. Alternatively, the detector 138 may be a homodyne or heterodyne receiver arranged to extract both magnitude and phase information from the reflected signal. Herein a detectable signal is a signal with high enough amplitude to enable a valid measurement to be made, i.e. it is possible to discern the signal component from the noise components. The low power amplifier 136 may be a low noise semiconductor amplifier (e.g. a GaAs device, HEMT, MMIC or the like) capable of producing an output power level of up to 20 dBm and beyond. If it is not required to boost the measurement signal then it may be preferable for the low noise amplifier to be omitted from the design since any additional active component in the receiver line-up will introduce a component of noise into the measured signal.

The output from the low power amplifier unit 136 is fed into the input (first) port of a microwave circulator 140, whose function is to direct reflected power from the surgical instrument 104 directly to reflected power detector 138. The circulator 140 operates to allow power flow in a clockwise direction only. The power from the output of low power amplifier 136 is therefore diverted to the second port of the circulator 140 where it is directed towards the surgical instrument 104 via waveguide switch 124 and transmission cable 126. The third port of the circulator 140 is connected to the reflected power detector 138. Any reflected power received into the second port is diverted to the third port and is therefore received by the detector 138. Since substantially all the reflected signal itself is provided to the detector 138 (i.e. it is not coupled), a lower power input signal can be used, which can reduce or minimize the risk of the radiation causing damage to tissue due to higher than necessary power levels emanating from the surgical instrument 104.

The signal output from the third port of the circulator 140 is a function of the degree of impedance mismatch between the radiating blade of the surgical instrument 104 and the biological tissue or air.

In an alternative embodiment (not shown) the signal at the first port of the circulator 140 is sampled in order to compare the difference between the reflected signal and the incident signal. Another optional feature is a carrier or forward signal cancellation circuit (also not shown) which may be implemented between the first and third ports of circulator 140 in order to remove any breakthrough signal that occurs between those ports.

The reflected signal measured using reflected power detector 138 is fed into the analogue to digital converter 132, where the analogue voltage level is digitised and processed using microprocessor/DSP unit 116. Power level adjustments can therefore be made to the treatment channel A (e.g. via control signals $C_1$ and $C_3$) based on the detected measurement signal transmitted along measurement channel B before any high power radiation is delivered by the device. This may provide safe control of the emitted radiation field.

Microwave power delivery into tissue is manually activated using footswitch 142, which may be a single pedal. The footswitch 142 is connected to the microprocessor/DSP unit 116 via isolation circuit 144, whose function is to create DC isolation (or galvanic isolation) between the footswitch 142 that is attached to the user/surgeon and the apparatus 100 to effectively break any DC path that would otherwise exist and form a part of the circuit. The isolation circuit 144 may also condition the signal such that it is suitable for processing by the microprocessor/DSP unit 116, i.e. a press of the footswitch pedal may be converted into a voltage pulse of +5 V amplitude.

The microprocessor/DSP unit 116 controls the operation of the system by sending suitable control signals $C_1$, $C_2$ and $C_3$ to various components as discussed above. A user interface 146 communicates with the microprocessor/DSP unit 116 to enable a user to enter instructions, e.g. power level demand, duration, energy delivery, etc., and to provide a display of the status of the operation of the system or instrument.

In another alternative embodiment, the apparatus 100 may be adapted to provide dynamic impedance matching as described in WO 2004/047659. Thus, another pair of power couplers and a tuning filter may also be provided on the treatment channel A, whereby the impedance of the tuning filter is adjustable, e.g. by signals sent from microprocessor/DSP unit 116 based on signals from the couplers to match that of the tissue at the distal end of the surgical instrument 104. The tuning filter may be a stub tuner comprising of a plurality of tuning rods or posts, or may comprise of an arrangement of varactor diodes where the reactance is changed by adjustment of the voltage across the diodes.

Selectable Frequencies—Apparatus

Figure 2A:
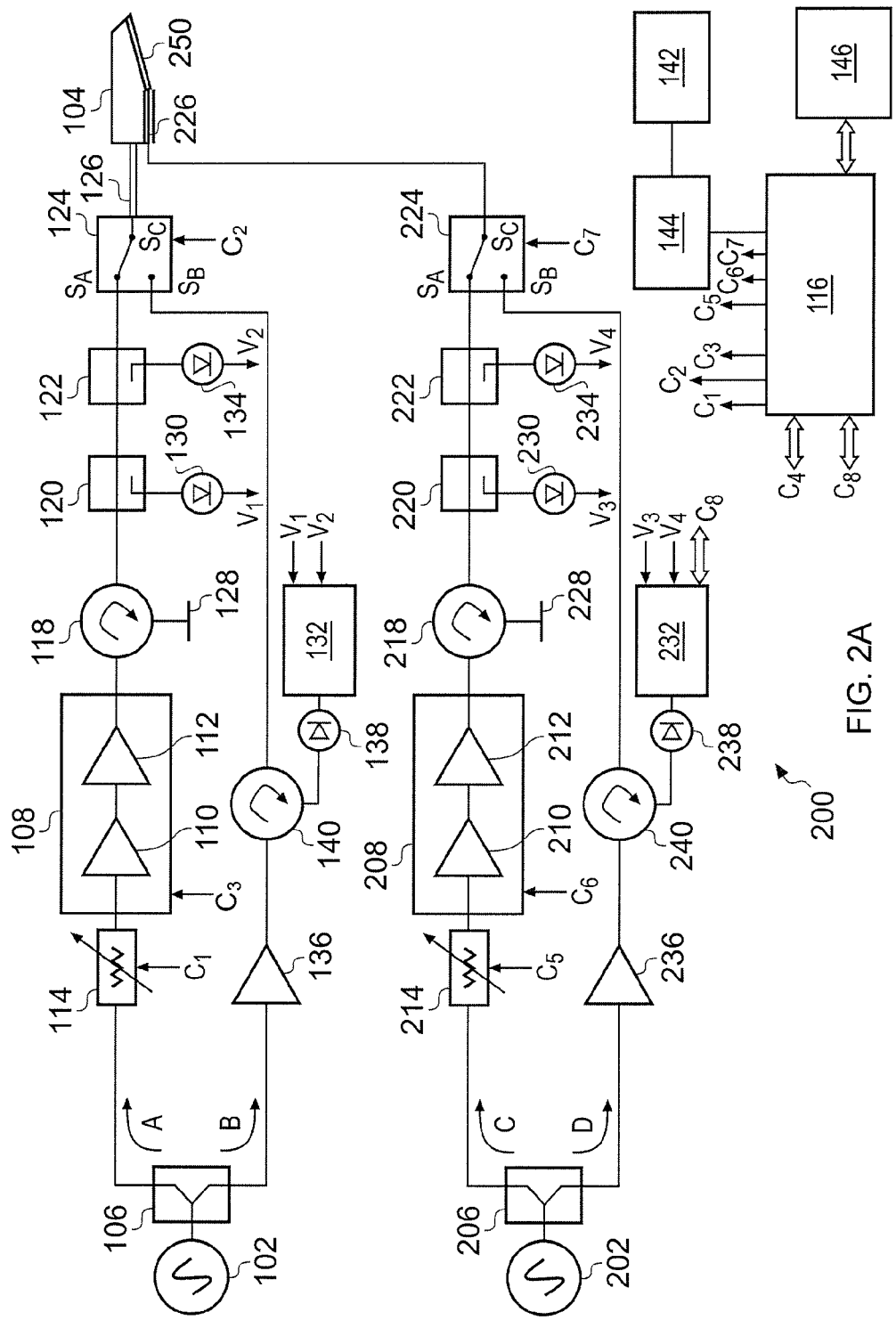
FIG. 2A is a schematic system diagram showing components of surgical cutting apparatus capable of delivering microwave radiation at two frequencies, and is an embodiment of both the first and second aspects of the invention.

FIG. 2A shows apparatus 200 that is an embodiment of the first and second aspects of the invention. The apparatus 200 has two microwave sources 102, 202, each of which are connected to a surgical instrument 104 by a two channel (high power treatment and low power measurement) arrangement that corresponds to the apparatus 100 shown in FIG. 1. Components in the line-up from the first source 102 are given the same reference number as components in FIG. 1 which provide the same function. The components in the line-up from the second source 202 are given similar reference numbers, except that they commence with a 2, e.g. splitter 206 performs a similar function to splitter 106.

The sources 102, 202 in the apparatus 200 shown in FIG. 2A generate microwave energy at different frequencies. The first source 102 generates energy at a higher frequency than the second source 202. For example, source 102 may provide a frequency of 10 GHz or more, e.g. between 10 GHz and 40 GHz. In this example 14.5 GHz or 24 GHz are preferred. The second source 202 is arranged to provide energy that will produce a large depth of penetration into the tissue to enable large blood vessels that may not be dealt with effectively using the first (higher microwave) frequency to be coagulated or sealed in an efficient manner to limit or prevent bleeding. The frequency may be less than 5 GHz, e.g. between 100 MHz and 5 GHz. In this example 2.45 GHz or 925 MHz are preferred.

The apparatus 200 shown in FIG. 2A effectively consists of two microwave circuits that are identical in construction except that they use components that operate at the different frequencies that are provided by their respective sources.

Thus, the first circuit corresponds to the two channels A, B discussed with reference to FIG. 1 and is not described again. For clarity, the connection between analogue to digital converter 132 and microprocessor/DSP unit 116 is indicated by control signal $C_4$.

The second circuit also has a treatment channel C and measurement channel D, and is arranged in a similar fashion to the apparatus shown in FIG. 1. It comprises a frequency source 202, power splitter 206, variable attenuator 214 (controlled by control signal $C_5$ from microprocessor/DSP unit 116), power amplifier unit 208 (including preamplifier 210 and power amplifier 212) controlled by control signal $C_6$ from microprocessor/DSP unit 116, circulator 218, 50Ω power dump load 228, forward power coupler 220, reflected power coupler 222, forward power detector 230 (delivering output $V_3$ to analogue to digital converter 232), reflected power detector 234 (delivering output $V_4$ to analogue to digital converter 232), waveguide switch 224 controlled by control signal $C_7$ from microprocessor/DSP unit 116, low power amplifier 236, low power circulator 240, detector 238 and cable assembly 226.

In both circuits, the signals from the three detectors 130, 134, 138, 230, 234, 238 are fed into respective analogue to digital converters 132, 232 and interfaced to a common microprocessor/DSP unit 116 (indicated by control signals $C_4$ and $C_8$ respectively). However, the invention may not be limited to this arrangement. For example, the apparatus 200 may use a common (e.g. single) analogue to digital converter for the two circuits, or the analogue to digital converters 132, 232 may form an integral part of microprocessor/DSP unit 116.

In the apparatus shown in FIG. 2A, the treatment channel C may be 'switched on' automatically using the information provided by the four detectors to deliver high levels of power at the second frequency. Alternatively, the waveguide switch 224 may be activated manually by the surgeon when he/she encounters a large bleed. In the latter case, the footswitch 142 may include two pedals to enable the surgeon to bring in (or turn on) the energy generated at the second frequency on demand. An arrangement comprising two pedals arranged side by side and mounted inside a single case may be provided with e.g. a blue pedal and a yellow pedal. Another embodiment may permit energy generation at the second frequency through the activation of a push button switch connected to the surgical instrument. The switch may be controlled by the surgeon as he/she maneuvers the blade inside the tissue.

The energy developed at the second frequency may be delivered using a half wavelength dipole, a quarter wavelength monopole, a half wavelength loop or a microstrip antenna arrangement. FIG. 2A shows the energy being delivered using a coaxial cable 226 which runs along the bottom edge of the surgical instrument 104 with the centre conductor feeding a microstrip structure 250 that is fabricated onto one of the (unmetallized) surfaces of the radiating blade. Blade structures for implementing the second aspect of the invention are discussed in more detail below with reference to FIGS. 4, 5 and 6.

Figure 2B:
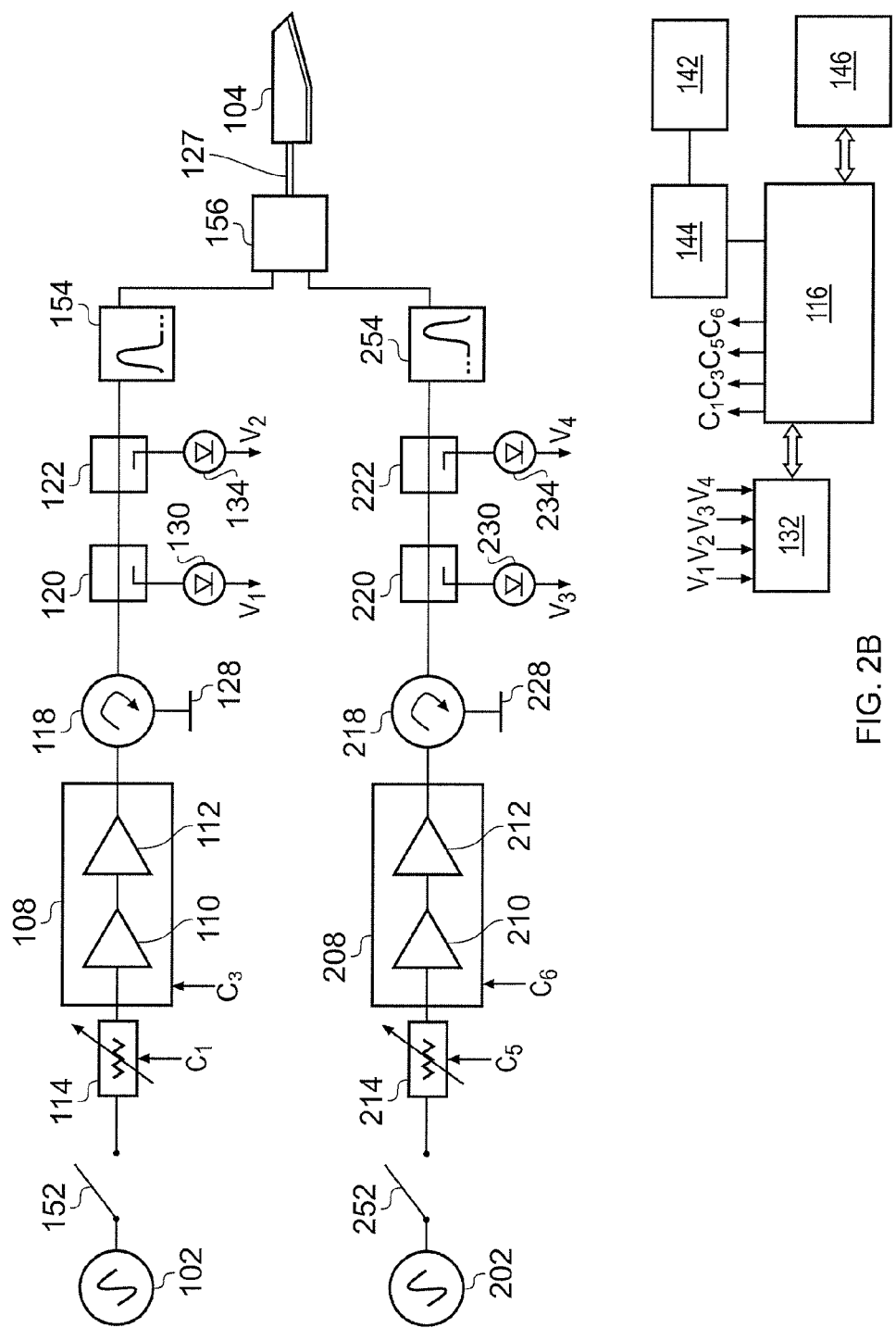
FIG. 2B is a schematic system diagram showing components of a surgical cutting apparatus capable of delivering microwave radiation at two frequencies which is another embodiment of the second aspect of the invention.

Another embodiment of the second aspect of the invention is shown in FIG. 2B. Features in common with FIG. 2A are given the same reference numbers and are not described again. In this embodiment a single analogue to digital converter 132 is used to convert the signals $V_1$, $V_2$, $V_3$ and $V_4$ received from the first and second circuits. In this embodiment each circuit only comprises a treatment channel.

The main difference between the embodiments shown in FIGS. 2A and 2B is the use of a common signal path 127 and filtering arrangement in FIG. 2B in place of the waveguide switches 124, 224 and separate signal paths 126, 226 in FIG. 2A. Thus, the amplified microwave signals from the first and second circuit are combined in power combiner 156 and transmitted to the respective antennas on surgical instrument 104 via common signal path 127, which may be a low loss coaxial cable. The first and second circuits have a first band pass filter 154 and a second band pass filter 254 respectively, which are arranged to transmit (or pass) energy at the frequency of their respective circuit and block energy at the frequency of the other circuit. Thus, the filters ensure that the reflected signals measured on each circuit are only those having the desired frequency of that circuit.

The first and second circuits can be activated and deactivated using simple switches 152, 252 e.g. controlled by footswitch 142 in the manner described above.

Variable Treatment Frequency

Figure 3A:
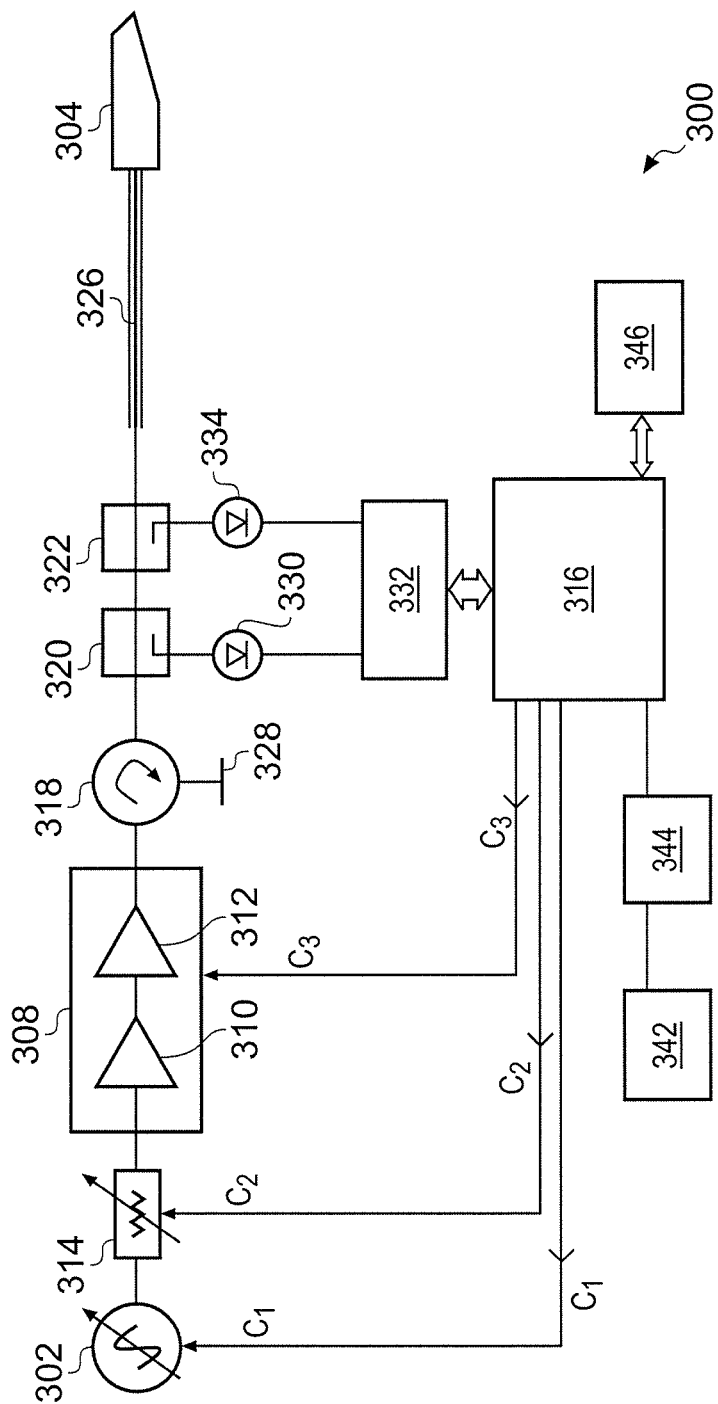
FIG. 3A is a schematic system diagram showing components of surgical cutting apparatus in which the frequency of microwave radiation delivered by the source is variable, and is an embodiment of the third aspect of the invention.

FIG. 3A shows apparatus 300 that is an embodiment of the third aspect of the invention. The apparatus 300 has a similar line-up to the apparatus 100 shown in FIG. 1, and the same components may be used to provide the corresponding functions. Thus, apparatus 300 comprises the following line-up between a frequency source 302 and surgical instrument 304: variable attenuator 314 (controlled by control signal $C_2$ from microprocessor/DSP unit 316), power amplifier unit 308 (including preamplifier 310 and power amplifier 312) controlled by control signal $C_3$ from microprocessor/DSP unit 316, circulator 318, 50.OMEGA. power dump load 328, forward power coupler 320, reflected power coupler 322, forward power detector 330 (delivering an output to analogue to digital converter 332), reflected power detector 334 (delivering an output to analogue to digital converter 332), and cable assembly 326. Similarly to FIG. 1, the apparatus 300 is controllable by a footswitch 342 connected to the microprocessor/DSP unit 316 via isolation circuit 344. A user interface 346 permits manipulation of the settings for the apparatus 300.

The third aspect of the invention is the provision of a single wideband power generation system. The system comprises a variable frequency source 302, which may be a voltage controlled oscillator or a frequency synthesiser which may contain a plurality of voltage controlled oscillators, whose output frequency is controlled based on a control signal $C_1$ from microprocessor/DSP unit 316; this signal may in fact be plurality of digital control lines, e.g. 8 lines, 16 lines or 32 lines. The source may be capable of generating any stable frequency in the range of interest, e.g. from 500 MHz to 24 GHz or more and it is desirable to be able to use the source to sweep over a range of frequencies within this band, i.e. between 1 GHz and 10 GHz.

Figure 3B:
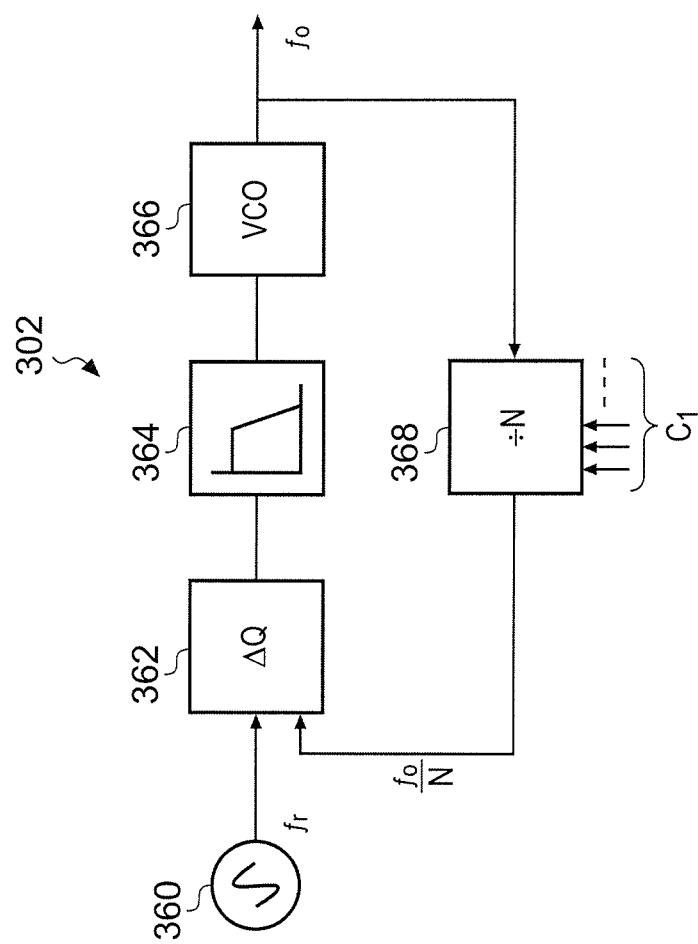
FIG. 3B is a schematic diagram of components in a frequency synthesiser.

In one embodiment, the source includes a frequency synthesiser. FIG. 3B is a schematic diagram of components in a source 302 that is a frequency synthesiser. Here the source includes a reference oscillator 360, e.g. a stable crystal oscillator, a phase comparator 362, a low pass filter 364, a voltage controlled oscillator (VCO) 366 and a programmable 'divide by N' divider 368 connected in a phase locked loop (PLL) arrangement.

The output frequency $f_o$ of the VCO 366 is a function of the applied voltage, i.e. the voltage on its varactor diode. The output from the phase comparator 362 is a voltage that is proportional to the phase difference between the signals at its two inputs; this controls the frequency of the VCO 366 so that the phase comparator input from the VCO via the divider 368 remains at a constant phase difference with the reference input $f_r$, i.e. so that those input frequencies are equal. The output frequency $f_o$ is thus maintained at $Nf_r$. The size of N may be variable e.g. based on the control signal $C_1$. The synthesiser may therefore be able to output a series of discrete frequencies across a range corresponding to different values of N. Adjacent frequencies in the series are separated by $f_r$.

Examples of commercially available frequency synthesisers that can be used in this embodiment include the LMPL-GSP range of dual frequency phase locked frequency synthesisers from GED. These products can produce frequencies over the range of between 100 MHz and 7 GHz. For higher frequencies, the VMESG series of broad bandwidth synthesisers from Elcom Technologies may be used. Devices in this series can operate up to 20 GHz. One product within this series provides a frequency range of between 50 MHz and 20 GHz with a 1 Hz resolution.

Power amplification unit 308 is arranged to be capable of delivering microwave power of up to and in excess of 300 W over a frequency range which lies between 500 MHz and 24 GHz, e.g. a range from 8 to 16 GHz. Table 2 lists devices manufactured by Thales Electronic Devices which may be suitable for this purpose:

TABLE 2

Amplifier components for wideband apparatus

| Product N° | Operational range (GHz) | Saturated output power (W) | Saturated gain (dB) |
|---|---|---|---|
| High power CW TWTs | | | |
| TL10055 | 6-18 | 150 | 30 |
| TL10058 | 7.5-18 | 200 | 30 |
| Mini/Micro TWTs | | | |
| TH4430S | 6-18 | 140 | 30 |
| TH4430C | 6-18 | 160 | 30 |

In this embodiment, the transmission cable 326 is a low loss coaxial cable. This can achieve the desired bandwidth without the possibility of the occurrence of moding. Waveguides may also be used, but generally have a more limited bandwidth than coaxial cables. Ridge waveguide structures may be considered as a means of increasing the frequency bandwidth from that achievable using standard rectangular waveguide.

It is desirable for apparatus 300 to have both a forward and reflected power coupler 320, 322 to enable the microprocessor/DSP unit 316 to calculate either magnitude, phase, or phase and magnitude information relating to the reflected power from the detected signals. This information can be used to enable selection of a suitable frequency for the energy delivered to the tissue, i.e. frequency is selected based on a detected condition of the tissue load, for example, it may be desirable to search for a null in reflected power in order to establish the optimum operating frequency that should be used.

In a preferred embodiment, the variable frequency of the source 302 may be scanned (swept) across a range. The forward and reflected power couplers 320, 322 and their respective detectors 330, 334 can record the response of the tissue across the frequency range, and can enable the microprocessor/DSP unit 316 to obtain information e.g. about the return loss of the apparatus 300 across the frequency range. Based on this information, an operating frequency of the source may be automatically selected. For example, the frequency at which an energy absorption peak occurs in a particular tissue type (or another material) may be selected in this manner. This arrangement may be advantageous in that the apparatus can be used with a variety of surgical instruments which may respond differently at different frequencies. Indeed, if the surgical instrument is a disposable item, this aspect of the invention may compensate for minor differences between instruments, which occur as part of the manufacturing process, or through temperature variations.

Selectable Frequencies—Surgical Instrument

The second aspect of the invention provides an apparatus where microwave energy having two different frequencies can be emitted from the same surgical cutting instrument. This can be achieved by providing two radiating structures, e.g. two antennas, on the surgical instrument.

FIG. 4 shows a first embodiment of a surgical instrument 400 with two radiating structures. The surgical instrument 400 is a rectangular block of waveguide (i.e. dielectric) material whose end is formed into a scalpel shape, with upper and lower angled sharp edges 402, 404 meeting at a point 406. The lower angled edge 404 is longer than the upper angled edge and forms a main blade of the surgical instrument.

The block of waveguide is coupled directly to the transmission cable of the apparatus that carries microwave energy at a first (higher) frequency. Metallization 408 is provided on the surfaces of the block of waveguide except at a narrow region 410 adjacent to the main blade (i.e. around lower angled edge 404). The unmetallized region 410 therefore acts as an antenna (e.g. radiating blade) for the microwave energy at the first frequency.

A coaxial cable 412 is mounted along the bottom of the block of waveguide. This coaxial cable 412 is the transmission cable of the apparatus that carries microwave energy at a second (lower) frequency. The centre conductor 414 of the coaxial cable is connected and feeds the microwave energy to a microstrip structure 416 which acts as an antenna for the microwave energy at the second frequency. In this embodiment, the microstrip structure 416 is mounted on a strip of dielectric material 418 provided on the layer of metallization 408 towards the lower angled edge 404. Thus, the field emitted by the microstrip structure 416 also emanates from the radiating blade of the surgical instrument. However, since it has a lower frequency, the depth of penetration of the field from the microstrip structure 416 is greater than that from the unmetallized region 410 itself.

In this embodiment, the layer of metallization 408 that forms a part of the radiating blade antenna used to deliver energy at the first frequency also acts as the ground plane for the energy produced at the second frequency. Thus, the dielectric material 418 lies between the layer of metallization 408 (acting as a first conductor or ground plane of the second antenna) and a second layer of metallization 416 which acts as a second (active) conductor and provides the microstrip design (not shown).

The centre conductor 414 of the coaxial cable is attached to the second conductor 416 using a solder contact/joint or other conductive mechanical means. The dielectric layer 418 may be a spray-on dielectric material that exhibits a low loss at the frequency of interest, or may be a sheet of dielectric material attached to the metallized portion of the radiating blade structure, for example, a sheet of Kapton may be used.

FIG. 5 shows a second embodiment of a surgical instrument 500 capable of launching energy into tissue at two different microwave frequencies. Similarly to the instrument shown in FIG. 4, surgical instrument 500 comprises a block of waveguide 501 whose end is formed into a scalpel shape having upper and lower angled sharp edges 502, 504 which meet at a point 506. The lower angled edge 504 is longer and provides the main cutting blade of the instrument 500. A layer of metallization 508 is provided on the surfaces of the block of waveguide 501 except at a region 510 adjacent to the lower angled edge 504. Similarly to FIG. 4, the block of waveguide is coupled directly to the transmission cable (waveguide) 520 of the apparatus that carries microwave energy at the first (higher) frequency. The unmetallized region 510 therefore acts as an antenna (e.g. radiating blade) for the microwave energy at the first frequency.

In this embodiment, the entire layer of metallization 508 is used as a second antenna to radiate energy at the second frequency into the biological tissue. The energy at the second frequency is provided via a coaxial cable 524, whose inner conductor 526 is connected and feeds energy at the second frequency to the layer of metallization 508. Thus, the surgical instrument 500 provides a monopole-type antenna structure with the whole outer portion of the block of waveguide 501 acting as a radiator or aerial. To enable the block of waveguide 501 to act as a radiator, an isolation layer 522 is inserted between the body of the transmission cable 520 and the block of waveguide 501 to provide electrical isolation between those components at the second (lower) frequency energy. The isolation layer 522 may be a dielectric material such as a ceramic material. The isolation layer 522 does not prevent radiation at the first frequency from being transmitted from the transmission cable 520 to the block of waveguide 501. The centre conductor 526 of the coaxial cable penetrates the isolation layer 522.

In alternative embodiments, it may be desirable to prevent or limit radiation of a microwave field at the second frequency from entering or propagating on/in particular sections or portions of the block of waveguide 501. This can be achieved by attaching a layer of insulating material to those regions. For example, a ceramic material or radiation absorbing material may be used.

Figure 6:
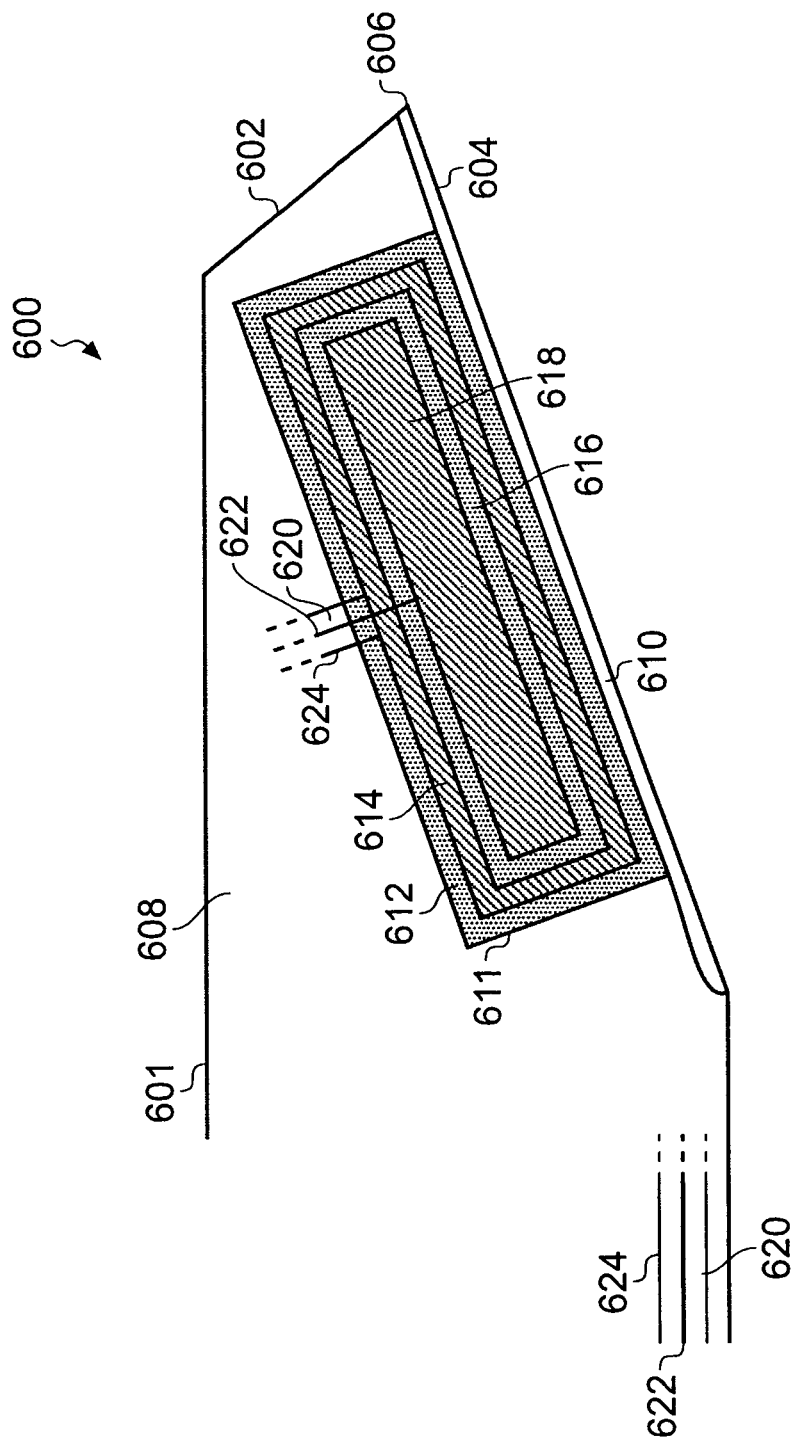
FIG. 6 is a side view of yet another surgical instrument having a blade and two antennas, and is another embodiment of the second aspect of the invention.

FIG. 6 shows a third embodiment of a surgical instrument 600 capable of launching energy into tissue at two different microwave frequencies. Similarly to the instrument shown in FIG. 4, surgical instrument 600 comprises a block of waveguide 601 whose end is formed into a scalpel shape having upper and lower angled sharp edges 602, 604 which meet at a point 606. The lower angled edge 604 is longer and provides the main cutting blade of the instrument 600. A layer of metallization 608 is provided on the surfaces of the block of waveguide 601 except at a region 610 adjacent the lower angled edge 604. Similarly to FIG. 4, the block of waveguide is coupled directly to the transmission cable (not shown) of the apparatus that carries microwave energy at the first (higher) frequency. The unmetallized region 610 therefore acts as an antenna (e.g. radiating blade) for the microwave energy at the first frequency.

In this embodiment, a self-contained patch antenna 611 is mounted on layer of metallization 608 adjacent to the unmetallized region 610. Thus, a region of the surface of the block of waveguide 601 is covered with a first dielectric material 612 that is attached to the blade by a suitable means (e.g. adhesive or the like), followed by a first layer of metallization 614 to act as the ground plane, followed by a second dielectric layer 616 to act as the medium through which the fields are propagated, followed by a second layer of metallization 618.

A coaxial cable 620 is mounted along the bottom of the block of waveguide 601. This coaxial cable 620 is the transmission cable of the apparatus that carries microwave energy at a second (lower) frequency. The centre conductor 622 of the coaxial cable is connected and feeds the microwave energy to the patch antenna 611 which therefore acts as an antenna for the microwave energy at the second frequency. The centre conductor 622 of the coaxial cable 620 is attached to the second layer of metallization and the outer conductor 624 of the coaxial cable is attached to the first layer of metallization 614. In this embodiment, the fields emanating from the edges of the second layer of metallization are used to cauterise or ablate the tissue structure.

Power Level Boost

Figure 7:
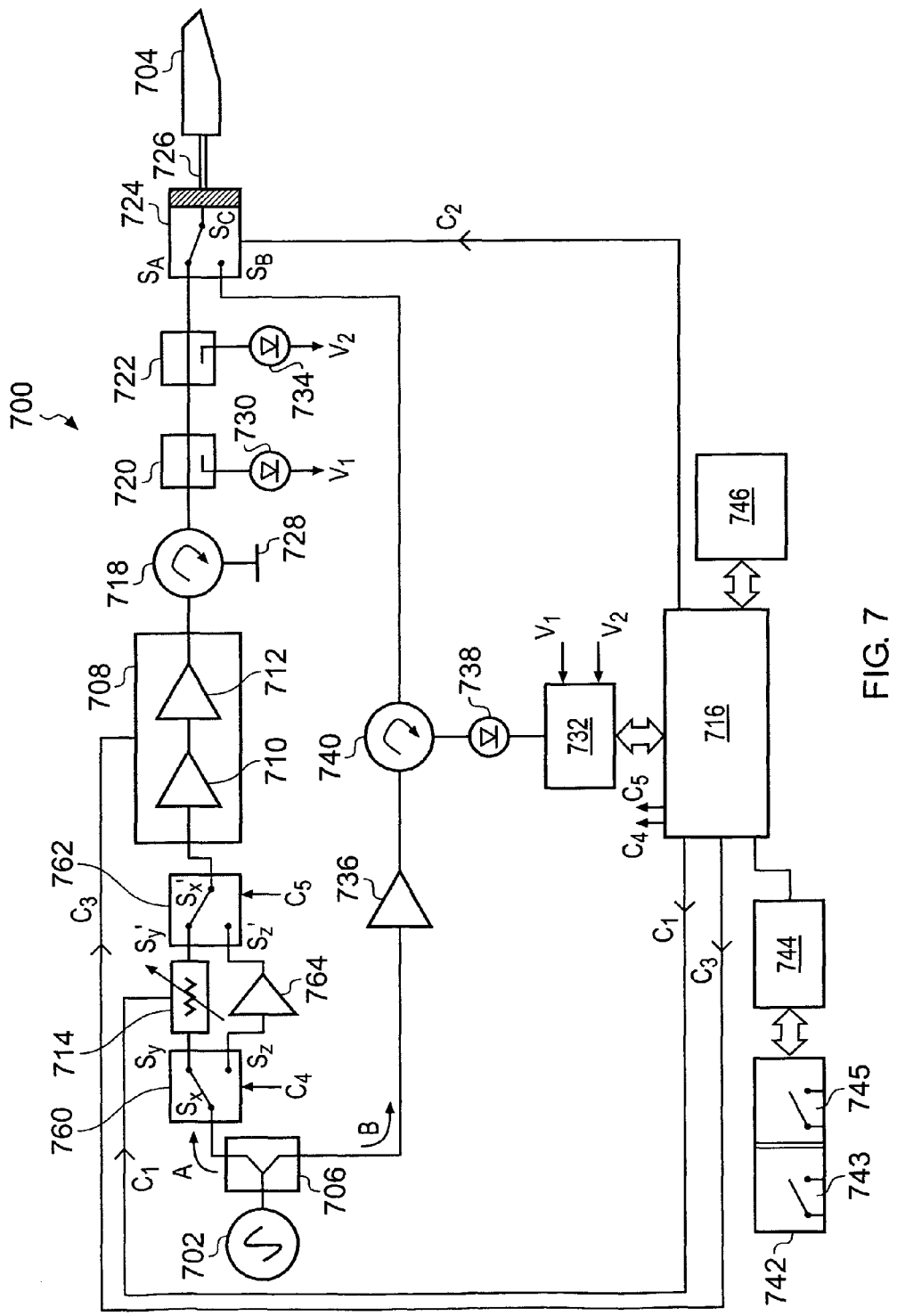
FIG. 7 is a schematic system diagram showing components of surgical cutting apparatus in which a treatment power level can be boosted, and is an embodiment of the first and fourth aspects of the invention.

FIG. 7 shows surgical cutting apparatus 700 that is an embodiment of the first and fourth embodiments of the invention. The apparatus 700 has a microwave source 702 which is connected to a surgical instrument 704 by a two channel (high power treatment and low power measurement) arrangement that corresponds to the apparatus 100 shown in FIG. 1. Components in the line-up between the source 702 and surgical instrument 704 which perform the same function as corresponding components in apparatus 100 are given similar reference numbers, except that they commence with a 7, e.g. splitter 706 performs a similar function to splitter 106.

Thus, the line-up comprises a frequency source 702, power splitter 706, variable attenuator 714 (controlled by control signal $C_1$ from microprocessor/DSP unit 716), power amplifier unit 708 (including preamplifier 710 and power amplifier 712) controlled by control signal $C_3$ from microprocessor/DSP unit 716, circulator 718, 50Ω power dump load 728, forward power coupler 720, reflected power coupler 722, forward power detector 730 (delivering output $V_1$ to analogue to digital converter 732), reflected power detector 734 (delivering output $V_2$ to analogue to digital converter 732), waveguide switch 724 controlled by control signal $C_2$ from microprocessor/DSP unit 716, user interface 746, low power amplifier 736, low power circulator 740, detector 738 and cable assembly 726. The functions of these elements are discussed above with respect to the first aspect and are not repeated here.

The fourth aspect of the invention is an adaptation of the apparatus whereby perfuse bleeding caused by large blood open vessels can be addressed by driving the amplification unit 708 hard to produce maximum power at the same frequency as used for normal operation.

In this embodiment, the apparatus 700 includes an overdrive signal path which bypasses the variable attenuator and boosts the input to the amplification unit 708 to drive the amplification unit 708 at full power. A pair of single-pole-two-throw switches 760, 762 is connected on treatment channel A on either side of the variable attenuator 714. The switches 760, 762 may be PIN switches and are arranged to adopt either a first configuration where the signal is directed through the variable attenuator 714 ('normal' operation) or a second configuration where the signal bypasses the variable attenuator 714 and is directed through a boost amplifier 764, which may be a low power amplifier ('boosted' operation). The switches 760, 762 are operated via control signals $C_4$, $C_5$ received from the microprocessor/DSP unit 716.

Thus, in normal operation the signal generated by frequency source 702 is connected to the input of variable attenuator 714 by connecting the common contact $S_x$ of first switch 760 to its first port $S_y$, and the output signal from variable attenuator 714 is connected to the amplification unit 708 by connecting the common contact $S_x'$ of second switch 762 to its first port $S_y'$. Thus, an attenuated version of the signal from the source 702 is used to drive amplification unit 708. This corresponds to the operation of treatment channel A discussed with reference to FIG. 1 above.

In boosted or 'overdrive' operation, switches 760, 762 adopt their second configuration following receipt of corresponding control signals $C_4$ and $C_5$ from the microprocessor/DSP unit 716. In the second configuration, the signal generated by source 702 is connected to the input of boost amplifier 764 by connecting the common contact $S_x$ of first switch 760 to its second port $S_z$, and the output signal from boost amplifier 764 is connected to the amplification unit 708 by connecting the common contact $S_x'$ of second switch 762 to its second port $S_z'$. The signal produced by source 702 is therefore re-routed such that it is amplified using low power amplifier 764 and the amplified signal used to drive amplification unit 708 into saturation or to enable it to produce maximum power at its output port.

The low power amplifier 764 may be optional. For example, if the amplitude of the signal produced by source 702 is of high enough amplitude to drive amplification unit 708 into saturation without additional gain being required, the low power amplifier 764 may be omitted from the line-up. In this instance second port $S_z$ of first switch 760 may be directly connected to second port $S_z$ of second switch 762. The variable attenuator 714 is bypassed to remove its insertion loss, which can be in excess of 1 dB even when its attenuation is set to a minimum value.

In an alternative embodiment the frequency source 702 produces a high enough power level to enable the second stage of amplification unit 708 to be driven into saturation when all (or a substantial amount) of the attenuation introduced by variable attenuator 714 is removed. Thus, the manually activated boost in this embodiment may be achieved by sending a control signal to the variable attenuator to instantly reduce the attenuation. In this embodiment, it is possible to omit the first and second switches 760 and 762 respectively, together with boost amplifier 764, from the microwave line-up shown in FIG. 7.

Similarly to the apparatus 100 shown in FIG. 1, a user operates the apparatus 700 using a footswitch arrangement 742, which is attached to the microprocessor/DSP unit 716 via an isolation circuit 744. In this embodiment, the footswitch arrangement comprises two pedals 743, 745. The first pedal 743 is arranged to control waveguide switch 724, i.e. to control switching between the treatment channel A and measurement channel B. The second pedal 745 is arranged to permit the user (e.g. surgeon) to select the configuration of the switches 760, 762 on the treatment channel, i.e. to select normal treatment or to drive the amplifier at full power ('boosted' treatment). Boosted treatment may be desirable when the user visually encounters a large bleed that cannot be dealt with effectively using the power level delivered during normal treatment.

Event Monitor

Figure 8:
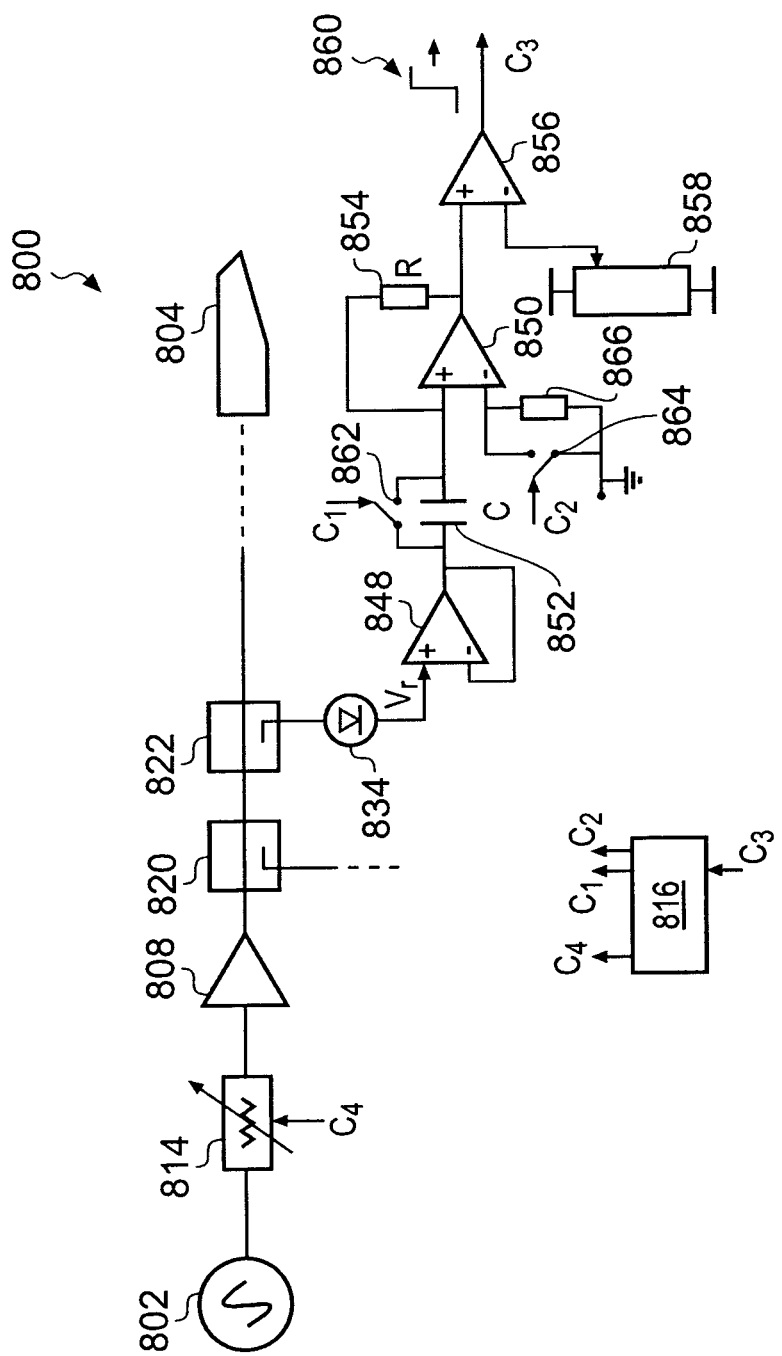
FIG. 8 is a schematic system diagram showing components of surgical cutting apparatus in which an analogue differentiator is provided to detect a signature event in the reflected power signal, and is an embodiment of the fifth aspect of the invention.

FIG. 8 shows the relevant parts of surgical cutting apparatus 800 that is an embodiment of the fifth aspect of the invention. The apparatus 800 has a microwave source 802 (e.g. oscillator) which is connected to a surgical instrument 804 by an arrangement that may correspond to the apparatus 100 shown in FIG. 1. Components in the line-up between the source 802 and surgical instrument 804 which perform the same function as corresponding components in apparatus 100 are given similar reference numbers, i.e., amplifier 808 performs a similar function as amplifier 108, forward power directional coupler 820 performs a similar function as forward power directional coupler 120, and variable attenuator 814 performs a similar function as variable attenuator 114.

According to the fifth aspect of the invention, the apparatus 800 includes a monitoring arrangement which is arranged to communicate a trigger signal $C_3$ to the microprocessor/DSP unit 816 if a certain event is detected in the reflected power signal obtained from reflected power coupler 822 and detected by detector 834. In this embodiment, the monitoring arrangement is an analogue implementation capable of monitoring the value of dv/dt of the detected reflected signal and generating a trigger signal when the monitored value exceeds a set threshold.

In detail, the detected signal (e.g. voltage $V_r$) from detector 834 is provided to a differentiator 850 via a buffer amplifier 848. The buffer amplifier 848 is interposed between the main apparatus line-up and the differentiator 850 to prevent the differentiator 850 from presenting an undesirable load to the detector 834. The differentiator circuit includes a capacitor 852 with a capacitance value C and a resistor 854 with resistance R arranged such that the output from differentiator 850 is $$-RC\frac{dV_r}{dt}.$$

This output is provided to a comparator 856, which is arranged to switch its output (e.g. to generate a step-like trigger signal 860) if the value of $$-RC\frac{dV_r}{dt}$$

(effectively the value of $dV_r/dt$ since that is the only variable) exceeds a threshold. In this embodiment, the comparator 856 compares $$-RC\frac{dV_r}{dt}$$

to the output from a potentiometer 858. The potentiometer 858 enables the threshold to be varied.

In this embodiment, the trigger signal 860 is generated if $dV_r/dt$ exceeds a certain value. A high value for $dV_r/dt$ (e.g. 5000 V/s) may indicate that a spitting event (e.g. violent ejection of tissue from the treatment site) is about to occur. The apparatus 800 is arranged to react to the trigger signal 860 to prevent the spitting event from occurring. If a trigger signal $C_3$ is received by the microprocessor/DSP unit 816, a response control signal $C_4$ is immediately sent to the variable attenuator 814, which instantly increases attenuation to reduce the power level delivered to the tissue to prevent the spitting event.

Reducing the power level to prevent the spitting event also stops the treatment from being as effective. It is therefore desirable for the response signal $C_4$ to operate the variable attenuator to ramp the power back up to a normal treatment level promptly after it is reduced to prevent the spitting event.

The microprocessor/DSP unit 816 may also be arranged to send control signals C1 and C2 to operate reset switches 862, 864 (e.g. MOSFET switches) which reset the differentiator after an event is detected. This ensures that the initial voltage across the capacitor 852 and resistor 866 is set to zero at the start of a new event.

In the embodiment discussed above, the detector 834 needs to be sensitive to the changes in the reflected signal which represent the monitored behaviour. In this case, the detector may need to sense a rapid change in $dV_r/dt$. Thus, if a diode detector is used, its rise/fall time must be short, e.g. 1 μs or less. For example, a tunnel diode based detector with a very fast pulse response may be used, e.g. product number ACTP1505N from Advanced Control Systems.

In use, the apparatus may deliver microwave radiation having frequency of 14.5 GHz or 24 GHz at 100 W during normal treatment, and the threshold value for $dV_r/dt$ at with the trigger signal is generated may be set to 4000 V/s. Thus, when a $dV_r/dt$ value of 5000 V/s is detected (e.g. corresponding to a rise of 5V in 1 ms in the reflected power signal), the power level is instantly reduced to 10 W, then ramped back up to 100 W over the following 100 ms. An overall treatment time may be set by a user before treatment commences. The apparatus may automatically compensate for the 'downtime' caused by preventing spitting events, e.g. so that a treatment time of 10 s may in fact take up to 100 s when regular power level reductions to prevent spitting are taken into account.

Figure 9:
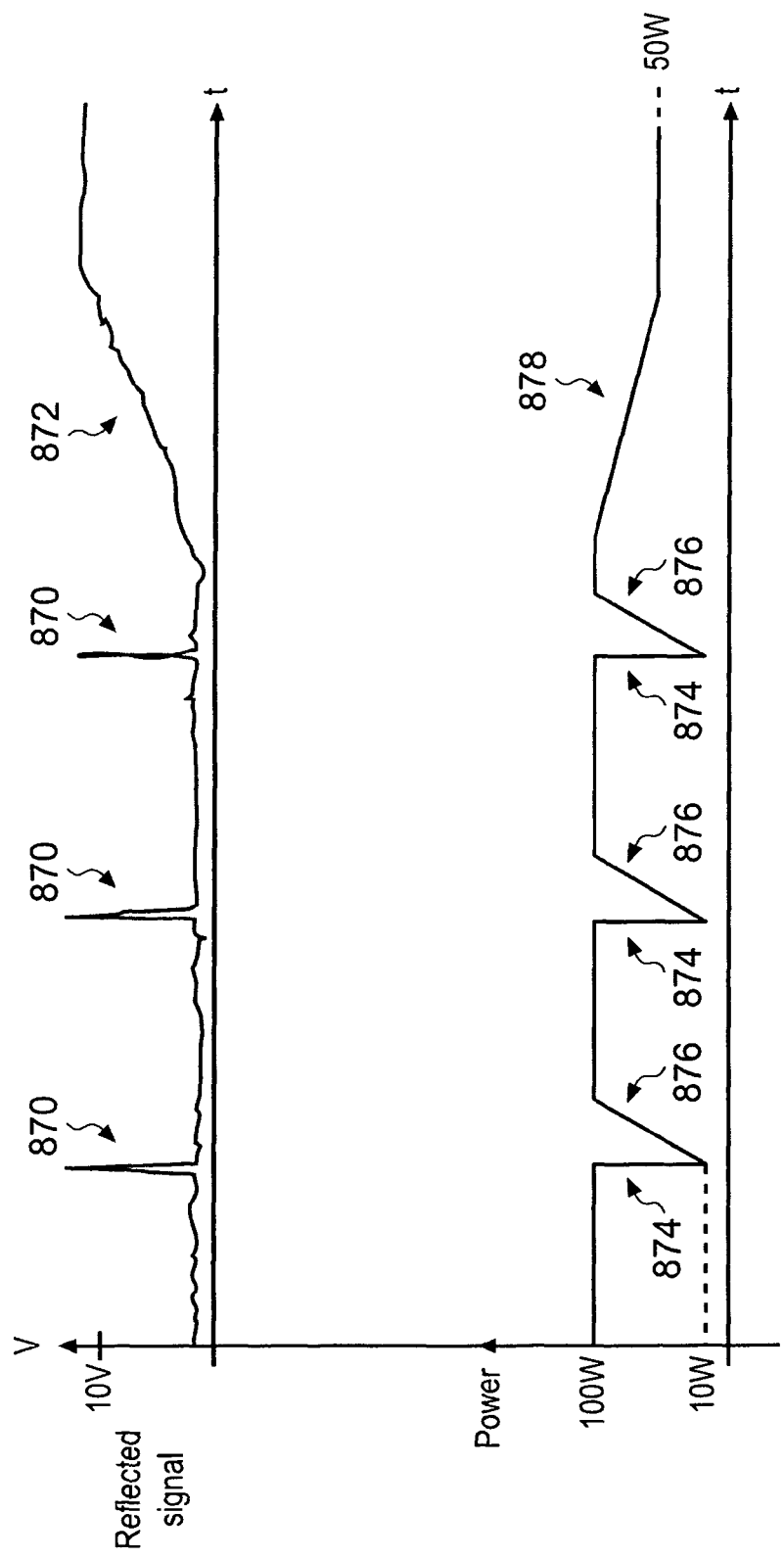
FIG. 9 is a chart showing how the power delivered to the antenna in the apparatus shown in FIG. 8 is altered depending on events detected in the reflected signal.

FIG. 9 is a graphical representation of how the power delivered by the apparatus can react to the detected reflected signal using the apparatus of the fifth aspect of the invention. The upper plot shown in FIG. 9 is the output from detector 834. There are three sharp voltage spikes 870 which indicate that a spitting event is about to occur and a gradual increase in voltage 872 which indicates a mismatch between the antenna and tissue, which may be an indication that treatment is effective. The lower plot uses the same time scale and shows the power delivered into the tissue. At positions corresponding to each of the voltage spikes 870, there are instant power drops 874 from 100 W to 10 W followed by relatively gradual ramp ups 876.

When the mismatch occurs, the power delivered falls away gradually 878 as the mismatch prevents full power from being coupled into the tissue.

The fifth aspect of the invention may also be used to detect other signature events, and therefore control other devices in the microwave line-up. For example, the monitoring arrangement may determine when the amplifier is to be driven into saturation or if a second frequency source is to be connected to the blade. In these cases, the monitoring arrangement may look for signature events associated with large open blood vessels. This particular signature may take the form of a constant level of voltage for a duration of time (time slot) that is greater than the average time for the system to produce a cut/coagulation over a predetermined distance in tissue. The size of each time slot can be established by experiment.

The invention claimed is:

1. A surgical instrument having:
   a cutting element having a blade with an edge for cutting biological tissue;
   a first antenna arranged to emit a substantially uniform microwave field of radiation at a first carrier frequency at the edge of the blade of the cutting element; and
   a second antenna arranged to emit a microwave radiation field at a second carrier frequency from the cutting element, the second carrier frequency being lower than the first carrier frequency,
   wherein the edge of the blade of the cutting element comprises a radiating portion for the first antenna, and
   wherein the second antenna is mounted adjacent the edge of the blade of the cutting element, whereby both antennas emit a substantially uniform microwave radiation field along the edge of the blade of the cutting element.

2. A surgical instrument according to claim 1, wherein the cutting element comprises a ceramic body having a coupling portion for attaching to a waveguide, and a blade portion which includes the blade having the edge for cutting biological tissue, wherein the radiating portion is integral with the blade portion and the coupling portion includes an impedance transformer.

3. Surgical cutting apparatus having:
   a microwave radiation source arranged to generate a first microwave radiation carrier signal having a first carrier frequency and a second microwave radiation carrier signal having a second carrier frequency;
   a surgical instrument having a cutting element comprising:
      a blade with an edge for cutting biological tissue,
      a first antenna connectable to the source to receive the first microwave radiation carrier signal and arranged to emit a substantially uniform microwave radiation field at the first carrier frequency along the edge of the blade of the cutting element, and
      a second antenna connectable to the source to receive the second microwave radiation carrier signal and arranged to emit from the surgical instrument a microwave radiation field at the second carrier frequency, wherein the second carrier frequency is lower than the first carrier frequency, wherein the edge of the blade of the cutting element comprises a radiating portion for the first antenna, and wherein the second antenna is mounted adjacent the edge of the blade of the cutting element, whereby both antennas emit a substantially uniform microwave radiation field along the edge of the blade of the cutting element.

4. Apparatus according to claim 3, wherein the source includes a first signal generator for producing the first microwave radiation carrier signal and a second signal generator for producing the second microwave radiation carrier signal, the first and second signal generators being connected to the first and second antennas respectively.

5. Apparatus according to claim 3 comprising a switch for selectively connecting the first antenna and/or second antenna to the source.

6. Apparatus according to claim 4, wherein the first and second signal generators are connectable to the surgical instrument via a common signal path, and wherein the surgical instrument receives the common signal path at a filtering arrangement arranged to deliver only energy at the first carrier frequency to the first antenna and only energy at the second carrier frequency to the second antenna.

7. Apparatus according to claim 3, wherein the apparatus further comprises:
   a reflected radiation detector connected between the source and the instrument to detect signals reflected back therefrom;
   a reflected power monitor arranged to detect a signature event in the reflected signals detected by the reflected radiation detector, wherein a signature event is a predetermined rate of change of reflected power or a constant level of reflected power detected during a certain time slot or for a certain duration; and
   a power level adjuster connected between the source and the instrument and arranged to automatically adjust a power level of the microwave radiation signals if the monitor detects a signature event.

8. Apparatus according to claim 7, wherein the monitor includes a differentiator arranged to
   measure a value of dv/dt (change of voltage with time) for the reflected signals, and
   compare the measured value to a threshold value, whereby the signature event is a value of dv/dt that is higher than a threshold.

9. Apparatus according to claim 7, wherein the power level adjuster is arranged to
   reduce the power level as soon as the signature event is detected, and
   ramp the power level back up in a recovery time period after the reduction in power level.

10. Apparatus according to claim 3, wherein the apparatus further comprises:
   a reflected radiation detector connected between the source and the instrument to detect signals reflected back therefrom; and
   a reflected power monitor arranged to detect a signature event in the reflected signals detected by the reflected radiation detector, wherein a signature event is a predetermined rate of change of reflected power or a constant level of reflected power detected during a certain time slot or for a certain duration,
   wherein the monitor is arranged to emit an audible or visual signal when a signature event is detected.

11. Apparatus according to claim 3, wherein the first carrier frequency is in the range 10 to 40 GHz.

12. Apparatus according to claim 3, wherein the second carrier frequency is in the range 100 MHz to 5 GHz.

13. Apparatus according to claim 3, wherein the microwave radiation source includes a wideband frequency oscillator able to emit an output signal over a range of frequencies, and wherein:
   the first carrier frequency is selectable to set up a resonant condition when the first antenna is in contact with biological tissue, and
   the second carrier frequency is selectable to set up a resonant condition when the second antenna is in contact with biological tissue.

14. Apparatus according to claim 3, wherein the microwave radiation source includes a wideband frequency oscillator able to emit an output signal over a range of frequencies, and wherein:
   the first carrier frequency is selectable to correspond to a frequency where an energy absorption peak occurs in biological tissue being treated when the first antenna is in contact with the biological tissue, and
   the second carrier frequency is selectable to correspond to a frequency where an energy absorption peak occurs in biological tissue being treated when the second antenna is in contact with the biological tissue.

* * * * *